(12) United States Patent
Kojima

(10) Patent No.: US 11,826,244 B2
(45) Date of Patent: Nov. 28, 2023

(54) ARTIFICIAL LENS CAPSULE

(71) Applicant: KYOTO PREFECTURAL PUBLIC UNIVERSITY CORPORATION, Kyoto (JP)

(72) Inventor: Kentaro Kojima, Kyoto (JP)

(73) Assignee: KYOTO PREFECTURAL PUBLIC UNIVERSITY CORPORATION, Kyoto (JP)

( * ) Notice: Subject to any disclaimer, the term of this patent is extended or adjusted under 35 U.S.C. 154(b) by 83 days.

(21) Appl. No.: 16/485,264

(22) PCT Filed: Feb. 13, 2018

(86) PCT No.: PCT/JP2018/004923
§ 371 (c)(1),
(2) Date: Aug. 12, 2019

(87) PCT Pub. No.: WO2018/147463
PCT Pub. Date: Aug. 16, 2018

(65) Prior Publication Data
US 2020/0000575 A1    Jan. 2, 2020

(30) Foreign Application Priority Data

Feb. 13, 2017 (JP) ................. 2017-024097

(51) Int. Cl.
*A61F 2/16* (2006.01)

(52) U.S. Cl.
CPC .............. *A61F 2/16* (2013.01); *A61F 2/1662* (2013.01); *A61F 2002/169* (2015.04);
(Continued)

(58) Field of Classification Search
CPC .. A61F 2/16; A61F 2/1662; A61F 2002/1681; A61F 2002/169–2002/16902;
(Continued)

(56) References Cited

U.S. PATENT DOCUMENTS 5,275,624 A * 1/1994 Hara ..................... A61F 2/1694
623/6.41
5,628,795 A    5/1997 Langerman
(Continued)

FOREIGN PATENT DOCUMENTS

EP    0732090 A1    9/1996
EP    2806828 A1    12/2014
(Continued)

OTHER PUBLICATIONS

International Search Report for related International Application No. PCT/JP2018/004923 dated Mar. 27, 2018.
(Continued)

*Primary Examiner* — Paul B Prebilic
(74) *Attorney, Agent, or Firm* — Renner, Otto, Boisselle & Sklar, LLP

(57) ABSTRACT

Provided is an intraocular lens affixing device which makes it possible to affix an intraocular lens of any kind with respect to the inside of an eye with a ruptured or deleted lens capsule. The intraocular lens affixing device 1 is provided with a device support portion (A) and an intraocular lens housing portion (B) connected to the device support portion (A). The device support portion (A) includes a frame 2 having a shape matching a ciliary sulcus 36. Also provided is an affixing kit for inserting an intraocular lens, the kit being provided with a) an intraocular lens affixing device; and b) an injector for injecting the affixing device.

42 Claims, 13 Drawing Sheets

(52) U.S. Cl.
CPC ............... *A61F 2002/16901* (2015.04); *A61F 2002/16902* (2015.04); *A61F 2002/169053* (2015.04); *A61F 2220/0025* (2013.01); *A61F 2230/0006* (2013.01); *A61F 2230/0008* (2013.01)

(58) Field of Classification Search
CPC .......... A61F 2002/16905–2002/169053; A61F 2220/0025; A61F 2230/0004–2230/0008; A61F 2230/0065; A61F 2250/001; A61F 2250/0039; A61F 2250/006–2250/0063; A61F 2/16015; A61F 2/1629
See application file for complete search history.

(56) References Cited

U.S. PATENT DOCUMENTS

| | | | | |
|---|---|---|---|---|
| 5,824,074 | A * | 10/1998 | Koch | A61F 2/1648 623/6.34 |
| 6,797,004 | B1 * | 9/2004 | Brady | A61F 2/1648 623/6.4 |
| 9,937,034 | B2 * | 4/2018 | Wanders | A61F 2/1648 |
| 10,441,411 | B2 * | 10/2019 | Sohn | A61F 2/1648 |
| 2005/0113914 | A1 * | 5/2005 | Miller | A61F 2/1629 623/6.37 |
| 2010/0204790 | A1 | 8/2010 | Whitsett | |
| 2011/0307058 | A1 | 12/2011 | Beer | |
| 2015/0202040 | A1 | 7/2015 | McCafferty | |
| 2015/0289970 | A1 * | 10/2015 | Akura | A61F 2/1629 623/6.37 |
| 2015/0305856 | A1 * | 10/2015 | Ichikawa | A61F 2/1613 623/6.44 |

FOREIGN PATENT DOCUMENTS

| | | |
|---|---|---|
| JP | 8317943 | 3/1996 |
| JP | 8317943 | 12/1996 |
| JP | 2003505196 A | 2/2003 |
| JP | 2013501598 A | 1/2013 |
| JP | 201490772 A | 5/2014 |
| JP | 2016174762 A | 10/2016 |
| WO | 2011020078 A1 | 2/2011 |
| WO | 2012/023133 A1 | 2/2012 |
| WO | 2013/112589 A1 | 8/2013 |
| WO | 2013/158942 A1 | 10/2013 |

OTHER PUBLICATIONS

Extended European Search Report and European Search Opinion for related European Application No. 18750891.6 dated Oct. 29, 2020.
Gong et al., Ultrasound Biomicroscopy Might Predict the Outcome of Phacoemulsification-Visco Dissection in Medically Controlled Primary Angle-Closure Glaucoma Eye With Extensive Peripheral Anterior Synechia, Front Med, Jul. 19, 2021, 8:705864.
Sugiura et al., Anatomy of the ciliary sulcus and the optimum site of needle passage for intraocular lens suture fixation in the living eye, J Cataract Refract Surg. 2018, 44(10), 1247-1253.
First Office Action for corresponding Japanese Application No. 2018-567542 dated Oct. 14, 2021 and its English Machine Translation.
Second Office Action for corresponding Japanese Application No. 2018-567542 dated Jan. 19, 2022 and its English Machine Translation.
Pereira FA and Cronemberger S, Ultrasound Biomicroscopic Study of Anterior Segment Changes after Phacoemulsification and Foldable Intraocular Lens Implantation., Ophthalmology (2003), vol. 110(9):1799-1806.
Marchini G, et al., Anterior segment changes during accommodation in eyes with a monofocal intraocular lens: High-frequency ultrasound study., J Cataract Refract Surg. (2008), vol. 34(6):949-956.

* cited by examiner (A) Inside an artificial lens capsule
(B) Inside a natural lens capsule (A)

(B)

(a) Prior Art  (b) Prior Art  (c) Prior Art (A) Prior Art — Inside natural lens capsule
(B) Prior Art — Ciliary sulcus fixation
(C) Prior Art — Suture to sclera
(D) Prior Art
(E) Prior Art
(F) Prior Art Ciliary sulcus fixation
Prior Art Inside natural lens capsule Suture to sclera
Prior Art Inside natural lens capsule
Prior Art

ARTIFICIAL LENS CAPSULE

TECHNICAL FIELD

The present invention relates to an invention in the ophthalmic field. More specifically, the present invention relates to a fixing device for fixing an intraocular lens implanted into an eye, i.e., artificial lens capsule. In one aspect, the device of the invention can be used in place of a lens with an impaired function due to an ophthalmic disorder such as cataract or if the lens capsule itself has also been lost. The device of the invention can also be used in place of a lens supporting tissue (lens capsule or the zonule of Zinn) with an impaired function due to an ophthalmic disorder such as lens capsule rupture, lens dislocation, or intraocular lens dislocation.

BACKGROUND ART

Cataract surgeries insert an intraocular lens as a replacement for a clouded lens. Generally, an intraocular lens is fixed inside the original support of the lens, lens capsule (intracapsular fixation).

An intraocular lens 3 comprising a lens support 30 depicted in FIG. 14 is commonly used as an intraocular lens used in such intracapsular fixation.

Each intraocular lens 3 depicted in FIGS. 14A, 14B, and 14C is implanted and fixed in a lens capsule in place of a removed lens. These intraocular lenses 3 comprise an optical portion 31 with a shape of a convex lens, and a plurality of pairs of lens supports 30, 30 extending outward from the outer circumferential portion of the optical portion 31. The intraocular lens 3 depicted in FIG. 14A is a three piece lens (consisting of an optical portion and two supports) prepared by joining the optical portion 31 and the supports 30 made with different materials. The intraocular lens 3 depicted in FIG. 14B has a plate-shaped support 30, and the intraocular lens 3 depicted in FIG. 14C is a one piece lens with the optical portion 31 and the support 30 made of the same material.

To fix the intraocular lens 3 within an eye (intracapsular fixation) in a conventional manner, the intraocular lens 3 is fixed within a lens capsule 35 so that the optical portion 31 of the intraocular lens 3 is positioned in the inner cavity of an incision formed on the anterior capsule of the lens capsule 35, and the peripheral end of the lens support 30 is positioned at the equator of the lens capsule 35 in place of a lens removed from within the lens capsule 35 by surgery as depicted in FIG. 1B (In the Figure, 40 is the cornea on the front surface of the eye ball, 41 is the ciliary body, 42 is the zonule of Zinn connected thereto, 43 is the sclera, and 44 is the retina).

If intracapsular fixation is not possible due to rupture of the lens capsule 35, damage to the zonule of Zinn 42 supporting the lens, or the like, an alternative method such as ciliary sulcus fixation or suture to the sclera is conventionally performed.

However, astigmatism correction lenses and multifocal intraocular lenses, which can be fixed with normal intracapsular fixation, cannot be fixed by such alternative methods.

FIG. 16, and FIGS. 17 and 18, depict an obstacle for a surgeon or patient when fixing an astigmatism correction lens inside the eye and when fixing a multifocal intraocular lens in the eye, respectively.

When fixing an astigmatism correction lens in the eye, intracapsular fixation requires the lens 3 to be fixed in the direction matching the direction of astigmatism by rotating the astigmatism correction lens 3 about the visual axis, as depicted in the top to bottom diagrams of FIG. 16A. However, ciliary sulcus fixation places an intraocular lens on the lens capsule 35, so that the type of intraocular lens is limited to the intraocular lens 3 with the support 30 depicted in FIG. 14A (ciliary sulcus fixation is not possible with the intraocular lens 3 in FIGS. 14B and 14C because the strength of the support 30 is insufficient). When a part of the lens capsule 35 is missing, the angle at which the lens 3 can be fixed is limited, as depicted in FIG. 16B. The lens 3 cannot be fixed while the support 30 of the lens 3 extends out from the missing portion as in the bottom diagram of FIG. 16B. As depicted in FIG. 16C, the type of lens is limited to the intraocular lens 3 with the support 30 depicted in FIG. 14A for suture to the sclera due to the procedure of suturing the lens support 30 to the sclera with a suture 32. The intraocular lenses 3 depicted in FIGS. 14B and 14C cannot be sutured due to the insufficient strength of the support 30 and the shape thereof. It is also very technically complex and difficult to fix the lens 3 after rotating the lens to a direction matching the astigmatism around the visual axis.

When fixing a multifocal intraocular lens in the eye, deviation of the visual axis to the forward or backward direction upon fixing the multifocal intraocular lens have a definitive effect on the success or failure of the surgery due to the optical property of dividing incident light for near and far focus. Meanwhile, means such as ciliary sulcus fixation and suture to the sclera cannot fix the intraocular lens 3 having the support 30 depicted in FIG. 14 at the same position on the visual axis as intracapsular fixation.

This is specifically described. FIG. 17B depicts the multifocal intraocular lens 3 fixed to the natural lens capsule 35, and FIG. 17A depicts the multifocal intraocular lens 3 fixed to a ciliary sulcus 36. If the multifocal intraocular lens 3 is fixed to the ciliary sulcus 36 as in FIG. 17A, the distance H1 between the lens 3 and the front side of the cornea 40 is different from the distance H2 between the intraocular lens 3 and the front side of the cornea 40 when the lens is fixed within the lens capsule 35 as in FIG. 17B. Therefore, incident light IL passing through the lens 3 is not focused on the retina 44.

FIG. 18B depicts the multifocal intraocular lens 3 fixed to the natural lens capsule 35 in the same manner as above, and FIG. 18A depicts the multifocal intraocular lens 3 sutured to the sclera 43. When the multifocal intraocular lens 3 is sutured to the sclera 43, the lens 3 cannot be fixed to the same position on the visual axis as capsular fixation in the same manner as FIG. 17A.

SUMMARY OF INVENTION

Solution to Problem

The present invention provides an intraocular lens fixing device which is capable of fixing any type of intraocular lens to an eye with a rupture of or loss of the lens capsule.

The present invention also provides an intraocular lens fixing device which is capable of fixing an intraocular lens to a direction matching the direction of astigmatism by rotating the lens about the visual axis, even when an astigmatism corrective intraocular lens is fixed.

The present invention further provides an intraocular lens fixing device which is capable of fixing an intraocular lens at the same position on the visual axis as intracapsular fixation, even when a multifocal intraocular lens is fixed in an eye.

The present invention also provides an intraocular lens fixing device having a structure with an excellent elastic deformability, which can be readily inserted into the eye with no risk of damaging tissue upon insertion.

The present invention further provides an intraocular lens fixing device that can reduce the manufacturing cost with a relatively simple configuration.

To achieve the objects described above, the present invention has the following features.

(1) An intraocular lens fixing device comprising:
   a device support (A); and
   an intraocular lens housing (B) coupled to the device support (A);
   wherein the device support (A) has a frame with a shape that conforms to a ciliary sulcus.
(2) The intraocular lens fixing device of item 1, wherein the intraocular lens housing (B) has a bag portion with an inner cavity formed thereon, and can store an intraocular lens rotatably about a visual axis within the bag portion.
(3) The intraocular lens fixing device of item 2, wherein the bag portion has a clamping portion for holding the intraocular lens.
(4) The intraocular lens fixing device of item 3, wherein the clamping portion is comprised of a pair, and the pair is configured to clamp the intraocular lens.
(5) The intraocular lens fixing device of item 3 or 4, wherein the clamping portion is comprised of a plurality of pairs, wherein the plurality of pairs are configured to clamp the intraocular lens.
(6) The intraocular lens fixing device of any one of items 3 to 5, wherein the clamping portion is elastically deformable in a direction of a visual axis and can elastically hold the intraocular lens.
(7) The method of any one of items 3 to 6, wherein the clamping portion is disposed at inner circumferential edges of a first clamping piece and a second clamping piece of the intraocular lens housing.
(8) The method of item 7, wherein the inner circumferential edges of the first clamping piece and the second clamping piece of the intraocular lens housing are within a range of less than 1.5 mm in a radial direction from an inner circumference of the intraocular lens housing.
(9) The method of item 8, wherein the inner circumferential edges of the first clamping piece and the second clamping piece of the intraocular lens housing are within a range of less than 0.5 mm in a radial direction from an inner circumference of the intraocular lens housing.
(10) The intraocular lens fixing device of any one of items 7 to 9, wherein a distance between clamping portions at the inner circumferential edges of the first clamping piece and the second clamping piece is 0.1 mm to 1.5 mm.
(11) The intraocular lens fixing device of item 10, wherein the distance between clamping portions at the inner circumferential edges of the first clamping piece and the second clamping piece is 0.3 mm to 1.2 mm.
(12) The intraocular lens fixing device of item 11, wherein the distance between clamping portions at the inner circumferential edges of the first clamping piece and the second clamping piece is 0.5 mm to 1.0 mm.
(13) The method of any one of items 7 to 12, wherein a distance between clamping portions of the inner circumferential edges of the first clamping piece and the second clamping piece is equal to or greater than a distance between portions other than the clamping portions of the intraocular lens housing.
(14) The intraocular lens fixing device of any one of items 1 to 13, wherein the shortest distance between a center of gravity of a cross-section of the frame and an outer surface of the frame is 0.05 mm to 0.3 mm.
(15) The intraocular lens fixing device of any one of items 2 to 14, wherein the bag portion has a space extending in a direction of the frame from the inner cavity.
(16) The intraocular lens fixing device of item 15, wherein the space can at least partially house an optical portion of the intraocular lens.
(17) The intraocular lens fixing device of any one of items 1 to 16, characterized by being used in an eye with a ruptured or lost lens capsule.
(18) The intraocular lens fixing device of any one of items 1 to 17, wherein the frame has an arcuate portion.
(19) The intraocular lens fixing device of item 18, wherein the frame has two or more arcuate portions.
(20) The intraocular lens fixing device of item 19, wherein the frame has three or more arcuate portions.
(21) The intraocular lens fixing device of any one of items 1 to 20, wherein the frame has an annular shape, a C-shape or an approximately circular shape.
(22) The intraocular lens fixing device of any one of items 1 to 21, wherein the device support has a length that contacts half of a circumference of a ciliary sulcus or greater.
(23) The intraocular lens fixing device of any one of items 1 to 22, wherein the intraocular lens housing (B) has an elastically deformable structure.
(24) The intraocular lens fixing device of any one of items 1 to 23, wherein the intraocular lens housing (B) has a slit that is long in a radial direction of the frame.
(25) The intraocular lens fixing device of any one of items 1 to 24, wherein the intraocular lens housing (B) is comprised of an elastically deformable material.
(26) The intraocular lens fixing device of any one of items 1 to 25, wherein the device support is deformable to a flat shape so as to allow insertion from an incision.
(27) The intraocular lens fixing device of any one of items 1 to 26, wherein the intraocular lens housing (B) has a C-shape, and an arcuate portion at a tip thereof.
(28) The intraocular lens fixing device of item 27, wherein the intraocular lens housing (B) has two or more arcuate portions.
(29) The intraocular lens fixing device of item 28, wherein the intraocular lens housing (B) has three or more arcuate portions.
(30) The intraocular lens fixing device of any one of items 1 to 29, wherein the device support has a size which allows insertion from an incision.
(31) The intraocular lens fixing device of any one of items 1 to 30, wherein there is a gap between a first plane formed by the frame and a second plane formed by the intraocular lens housing (B), the gap having a distance that does not change an angle of refraction when an intraocular lens is fixed to a natural lens capsule.
(32) The intraocular lens fixing device of item 31, wherein the gap is 1 mm to 3 mm.
(33) The intraocular lens fixing device of any one of items 1 to 32, wherein a cross-sectional shape of the frame is substantially circular or oval.
(34) The intraocular lens fixing device of any one of items 1 to 33, wherein an outer surface of the frame has a curvature (curved portion).

(35) The intraocular lens fixing device of any one of items 1 to 34, wherein the intraocular lens housing (B) has an extended portion extended inward from a frame of the device support, and a holding piece extended inward from an inside end of the extended portion.
(36) The intraocular lens fixing device of item 35, wherein the holding piece has a pair of clamping pieces arranged in parallel to hold an intraocular lens.
(37) The intraocular lens fixing device of item 35 or 36, wherein the extended portion is inclined at an angle of 30 degrees to 60 degrees with respect to a first plane formed by the frame of the support.
(38) The intraocular lens fixing device of any one of items 1 to 37, having a shape which allows injection with an injecting instrument.
(39) A fixing kit for inserting an intraocular lens, comprising:
a) the intraocular lens fixing device of any one of items 1 to 38; and
b) an injecting instrument for injecting the fixing device.
(40) A method of inserting an intraocular lens into an eye, comprising:
a) inserting the intraocular lens fixing device of any one of items 1 to 38 into an eye and making a frame of the device support (A) conform to a ciliary sulcus; and
b) fixing an intraocular lens to the intraocular lens housing (B) of the intraocular lens fixing device.
(41) The method of item 40, wherein the intraocular lens fixing device is inserted from an incision on an eye.
(42) The method of item 41 or 26, wherein the intraocular lens fixing device is inserted into an eye using an injecting instrument.
(43) The method of any one of items 40 to 42, wherein the step of inserting the intraocular lens fixing device from an incision on an eye comprises providing an injecting instrument for injecting the intraocular lens fixing device and inserting an intraocular lens fixing device into an eye from an aperture on the eye using the injecting instrument.
(44) The method of any one of items 40 to 43, the method comprising:
a) providing a first injecting instrument for injecting the intraocular lens fixing device of any one of items 1 to 38;
b) inserting the intraocular lens fixing device into an eye from an incision on the eye using the first injecting instrument;
c) providing a second injecting instrument for injecting an intraocular lens; and
d) housing the intraocular lens in the intraocular lens housing (B) of the intraocular lens fixing device from the incision on the eye using the second injecting instrument.

The present invention is intended so that one or more of the aforementioned features can be provided not only as the explicitly disclosed combinations, but also as other combinations. Additional embodiments and advantages of the present invention are recognized by those skilled in the art by reading and understanding the following detailed descriptions as needed.

Advantageous Effects of Invention

The present invention has the following effects.

Since the intraocular lens fixing device of the invention has a frame with a shape that conforms to a ciliary sulcus, the device of the invention can be fixed inside an eye with a ruptured or lost lens capsule, and can house and fix any type of intraocular lens in an intraocular lens housing of the device. The device structure can also be simplified and has excellent deformability. Since a frame is used to fix a device to a ciliary sulcus, the structure can also be simplified to reduce manufacturing cost.

Furthermore, if an intraocular lens housing is configured to have a bag portion with an inner cavity formed thereon to be able to store an intraocular lens rotatably about the visual axis in the bag portion, the intraocular lens can be rotated within the bag portion of the housing to change the fixation angle so as to correct the astigmatic axis of a patient when fixing an astigmatism corrective intraocular lens with an additional function of astigmatism correction with the device.

The present invention attains an improved effect over conventional intraocular lens fixing devices.

For example, many conventionally proposed devices are embedded into the lens capsule, but the prevent invention is advantageous over such devices in that the invention can be applied inside an eye with a ruptured or lost lens capsule.

For devices that can be applied inside an eye with a ruptured or lost lens capsule, optical parts used in the devices have a specific shape to conform to the devices so that various types of intraocular lenses depicted in FIGS. 14 and 15 cannot be fixed to the devices, but the present invention is also compatible with such shapes. Especially when an astigmatism correction lens is fixed inside an eye, a lens needs to be fixed to a device in a direction matching the direction of astigmatism by rotating the astigmatism correction lens about the visual axis as described above. Meanwhile, conventional devices cannot rotatably store an intraocular lens, and an intraocular lens can also shift after fixing the lens to the device, but this has been overcome by the present invention. Furthermore, a multifocal intraocular lens cannot be suitably fixed inside a device for a configuration where an intraocular lens moves in the direction of the visual axis inside the device. A device provided with a fixing support also has a risk of damaging tissue when inserting the device into an eye, and the structure of such a device is complex with high manufacturing cost. Meanwhile, the present invention is advantageous in that this can also be addressed.

BRIEF DESCRIPTION OF DRAWINGS

FIGS. 2(A) and 2(B) show an intraocular lens rotated about a visual axis in an intraocular lens housing of the device.

FIG. 3 FIGS. 3(A), 3(B), and 3(C) are a perspective view, front view, and side view of the intraocular lens fixing device depicted in FIG. 1(A).

FIG. 4 FIGS. 4(A), 4(B), and 4(C) are cross-sectional views of an intraocular lens housed in the intraocular lens fixing device depicted in FIG. 2(A). FIG. 4(D) is a plan view depicting the inner circumferential edge of an intraocular lens housing.

FIG. 19(A) is a diagram depicting the intraocular lens fixing device ver. 1.

FIG. 20 is a diagram depicting the intraocular lens fixing device ver. 3.

DESCRIPTION OF EMBODIMENTS

Figure 1:
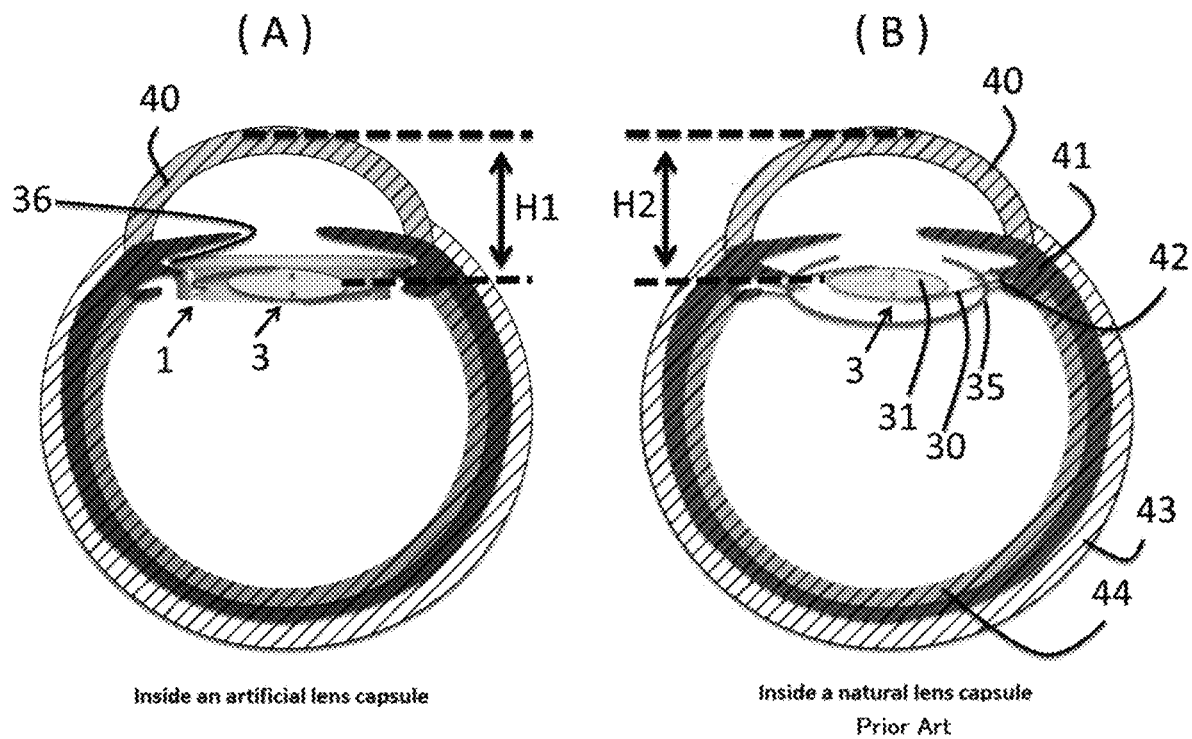
FIG. 1(A) is a cross-sectional view showing the intraocular lens fixing device according to an embodiment of the invention when installed.
FIG. 1(B) is a cross-sectional view showing an intraocular lens fixed within a natural lens capsule.

The present invention is explained hereinafter while providing the best modes thereof. Throughout the entire specification, a singular expression should be understood as encompassing the concept thereof in the plural form, unless specifically noted otherwise. Thus, singular articles (e.g., "a", "an", "the", and the like in the case of English) should also be understood as encompassing the concept thereof in the plural form, unless specifically noted otherwise. Further, the terms used herein should be understood as being used in the meaning that is commonly used in the art, unless specifically noted otherwise. Therefore, unless defined otherwise, all terminologies and scientific technical terms that are used herein have the same meaning as the general understanding of those skilled in the art to which the present invention pertains. In case of a contradiction, the present specification (including the definitions) takes precedence.

As used herein, terms of approximation such as "about", "substantially", "essentially", and "approximately" (not limited thereto) mean that the feature mentioned as "about", "substantially", or the like does not need to be strictly specified explicitly in the Claims, and can vary to some extent. The degree to which the feature can vary would depend on the size of change incorporated into the feature and whether the changed feature can be recognized by those skilled in the art as still having the properties and functions of the feature prior to the change. In general, the numerical values herein that are changed by a term of approximation such as "about" can vary by at least ±10% from the specified value in view of the above discussion.

The definition of the terms and the basic technical matters that are particularly used herein are appropriately explained hereinafter.

(Intraocular Lens Fixing Device)

The present invention provides a device for fixing an intraocular lens in the eye.

As used herein, "intraocular lens" has the same meaning as the conventional meaning in the art. An intraocular lens is used in place of a cloudy lens by a cataract surgery. Alternatively, an intraocular ocular lens can be embedded into an eye of a patient while holding the patient's own lens to improve the vision of the patient. Both monofocal IOLs and multifocal IOLs are known. Monofocal IOLs provide the ability to focus on a single focal point, while multifocal IOLs can provide the ability to focus on a plurality of (generally two) focal points to provide some degree of accommodation, generally known as pseudoaccomodation.

As used herein, "intraocular lens fixing device" refers to any device for fixing an intraocular lens in an eye. Generally, an intraocular lens fixing device comprises a device support for supporting the device itself and an intraocular lens housing. The device support and the intraocular lens housing can be formed as separate parts or integrally. The device is advantageously used in an eye with a ruptured or lost lens capsule in the present invention. A fixing device preferably has a shape which allows injection by an injecting instrument because the device is inserted using an injecting instrument in normal surgeries, but the shape is not limited thereto.

As used herein, "device support" refers to a portion that is used for an intraocular lens fixing device, having a function of fixing the device itself in an eye. A device support can have any shape, such as a polygonal shape (triangular, square, pentagonal, hexagonal, heptagonal, octagonal, etc.), circular shape, or C-shape, as long as a device can be fixed in the eye. A device support can preferably comprise a "frame" with a shape that conforms to a ciliary sulcus. As used herein, "frame" refers to any member that surrounds the device structure such as the device of the invention. The frame of the invention can have any shape depending on the shape of the device support, is made of any material (e.g., biocompatible material), and can have a polygonal shape (triangular, square, pentagonal, hexagonal, heptagonal, octagonal, etc.), circular shape, C-shape, or the like. The diameter of a device support is preferably 10 mm or greater, more preferably 11 to 14 mm. Such a dimension matches a general case where the outer diameter of a ciliary sulcus of a human eye is about 11 mm. The dimension can be determined by considering the state in which a device is implanted into an eye. The shape of a support device can be annular or arcuate. Alternatively, the shape is preferably a point symmetric shape (e.g., polygonal shape including circular, oval, and triangular shape) because such a shape alleviates the effect (e.g., tissue damage or elicitation of inflammation) on the ciliary sulcus or the like. In one embodiment, a frame or a device support is annular or has a C-shape or approximately circular shape and advantageously has a length that contacts half of the circumference of a ciliary sulcus or greater. In a preferred embodiment, there is a gap (e.g., 1 mm to 3 mm) between a first plane formed by a frame and a second plane formed by an intraocular lens housing (B), the gap having a distance that does not change an angle of refraction when the intraocular lens is fixed to a natural lens capsule. This allows any intraocular lens to be appropriately disposed. In an exemplary embodiment, the cross-sectional shape of a frame is substantially circular or oval. Preferably, the outer surface of a frame has a curvature (curved portion). Injury to the biological body can be reduced or eliminated by having such a curvature. In one preferred embodiment, the intraocular lens housing (B) has an extended portion extended inward from a frame of the device support, and a holding piece extended inward from an inside end of the extended portion. Typically, the holding piece has a pair of clamping pieces arranged in parallel to hold an intraocular lens. In an exemplary embodiment, the extended portion is inclined at an angle of 30 degrees to 60 degrees (e.g., 30 degrees, 35 degrees, 40 degrees, 45 degrees, degrees, 55 degrees, 60 degrees, or any angle therebetween) with respect to a first plane formed by a frame of the support.

As used herein, "intraocular lens housing" refers to a portion for housing an intraocular lens. Any shape can be used as long as an intraocular lens can be housed. An intraocular lens housing can hold an optical portion or support of an intraocular lens, serving the role of preventing the fall to the vitreous body. A circle, arc, oval as well as polygonal shapes including triangle and square and the like can be used as the shape of an intraocular lens housing. Preferably, a shape that is similar to the shape of an optical portion of an intraocular lens, which is considered to have the least effect of disturbing the transmittance of a light beam, is considered the most advantageous for holding an optical lens and correcting vision. Since the size of an optical portion of an intraocular lens is generally about 5 to 7 mm, the size, in one embodiment, is greater than the optical portion of the intraocular lens, or, even if smaller than the optical portion of the intraocular lens, is preferably 3 mm or greater and more preferably 4 to 7 mm as the effective optical portion.

A device support and an intraocular lens housing can be coupled in any manner. The coupling methodology is not limited, but examples thereof include physical bonds, chemical bonds using an adhesive or the like. In one aspect, the present invention provides an intraocular lens fixing device with a novel shape. The intraocular lens fixing device of the invention comprises a device support and an intraocular lens housing coupled to the device support, and the device support has a frame with a shape that conforms to a ciliary sulcus. Since the present invention has a frame with a shape that conforms to a ciliary sulcus, the device of the invention can be fixed in an eye with a ruptured or lost lens capsule, such that an intraocular device of any shape can be applied to a subject. In a preferred embodiment, a device support is deformable to a flat shape so as to allow insertion from an incision, and the device support advantageously has a size which allows insertion from an incision.

In one embodiment, an intraocular lens housing has a bag portion with an inner cavity formed thereon, and can store an intraocular lens rotatably about a visual axis within the bag portion. In an exemplary embodiment, the intraocular lens housing can have a slit that is long in a radial direction of the frame and can be comprised of an elastically deformable material. An intraocular lens fixing device is imparted with plasticity by having a slit on an intraocular lens housing. As a result, the time required for insertion from an incision wound to a deeper part inside an eye can be reduced.

As used herein, "bag portion" refers to any portion that can at least partially envelop a subject to be housed such as an intraocular lens. An inner cavity is formed. In a preferred embodiment, an intraocular lens can be stored rotatably about a visual axis within the bag portion. Such a rotatably shape or configuration can be materialized by those skilled in the art with an appropriate material and shape. Examples thereof include those described in each embodiment.

In one embodiment, a clamping portion can be provided to a bag portion. As used herein, "clamping portion" can refer to any portion with a shape or configuration that can hold a target of clamping (e.g., intraocular lens) in a clamping manner. Typically, a clamping portion consisting of a pair of parts (as used herein, this portion of a clamping portion is especially referred to as a "clamping piece"). The portions constituting the pair of the clamping portion are disposed at positions to clamp each other, and are configured to be movable to clamp a target. This allows a target (e.g., intraocular lens) to be fixed after the target is housed. The pair portion can be a single pair or a plurality of pairs. This portion is also known as an intraocular lens insertion groove in view of the shape and function thereof. Such fixation can strongly fix an intraocular lens in an eye after housing a target to prevent the intraocular lens from shifting. This stabilizes the vision and improves the Quality of Life. The region where the bag portion is or the like can have any shape, as long as an intraocular lens can be housed. For example, a shape having a space extending from an inner cavity to the direction of a frame or the like is advantageously provided. Such a configuration allows the space to at least partially house an optical portion of an intraocular lens.

In one embodiment, the clamping portion used in the present invention is elastically deformable in a direction of a visual axis. Such a deformable configuration allows the intraocular lens to be elastically held.

While biocompatible polymethyl methacrylate (PMMA), polyethyl methacrylate (PEMA), polyhydroxyethyl methacrylate (PHEMA), polypropylene (PP), polyimide, polyvinylidene fluoride (PVDF) or other fluororesin, thermoplastic elastomer, silicone, acrylic material, or the like is preferably used as a material that can be used in the device of the invention, a transparent, elastic, and processable material, e.g., a biopolymer such as collagen, plastic fiber thread such as nylon, or the like can also be suitably used. Furthermore, a more biocompatible material derived from an organism such as fibronectin, chondroitin sulfate, hyaluronic acid, or heparin can be adsorbed or chemically bound to the material surface of an assistive tool. For such a member, each member can be made of the same material or different materials, or some of the members can be made of the same material while others are made of different materials.

In one embodiment, a frame has an arcuate portion. In a preferred embodiment, a frame has two or more, three or more, or four or more arcuate portions. In another embodiment, a frame can have 1, 2, 3, 4, 5, 6, 7, 8, 9, 10, 11, 12, 13, 14, 15, 16, 17, 18, 19, 20, or more arcuate portions. In a specific embodiment, a frame can have a shape other than arcuate that is not prone to being obstructed to pass a corneal incision wound. Examples of a shape that is not prone to being obstructed to pass include, but are not limited to, portions with an obtuse angle. Examples of an obtuse angle include, but are not limited to, 95 degrees, 100 degrees, 105 degrees, 110 degrees, 115 degrees, 120 degrees, 125 degrees, 130 degrees, 135 degrees, 140 degrees, 145 degrees, 150 degrees, 155 degrees, 160 degrees, 165 degrees, 170 degrees, and 175 degrees. Having such a shape significantly reduces being obstructed to pass a corneal incision wound when inserting the device of the invention from a corneal incision wound, such that insertion is facilitated.

In one embodiment, an intraocular housing has a C-shape and has an arcuate portion at a tip thereof. In a preferred embodiment, an intraocular lens housing has two or more, three or more, or four or more arcuate portions. In another embodiment, the intraocular lens housing can have 1, 2, 3, 4, 5, 6, 7, 8, 9, 10, 11, 12, 13, 14, 15, 16, 17, 18, 19, 20, or more arcuate portions. In a specific embodiment, an intraocular lens housing can have a shape other than arcuate that is not prone to being obstructed to pass a corneal incision wound. Examples of a shape that is not prone to being obstructed to pass include, but are not limited to, portions with an obtuse angle. Examples of an obtuse angle include, but are not limited to, 95 degrees, 100 degrees, 105 degrees, 110 degrees, 115 degrees, 120 degrees, 125 degrees, 130 degrees, 135 degrees, 140 degrees, 145 degrees, 150 degrees, 155 degrees, 160 degrees, 165 degrees, 170 degrees, and 175 degrees. Having such a shape significantly reduces being obstructed to pass a corneal incision wound when inserting the device of the invention from a corneal incision wound, such that insertion is facilitated.

As used herein, "inner circumferential edges of a first clamping piece and a second clamping piece of the intraocular lens housing" refers to a portion at the inner circumferential edge of an intraocular lens housing. An intraocular lens fixing device may or may not contact an intraocular lens at the inner circumferential edge. For example, this refers to a portion marked with a box in FIGS. 4(B) to 4(C) and the portion indicated by the lattice in FIG. 4(D).

In a specific embodiment, inner circumferential edges of a first clamping piece and a second clamping piece of the intraocular lens housing are in a range of less than 1.5 mm, 1.4 mm, 1.3 mm, 1.2 mm, 1.1 mm, 1 mm, 0.9 mm, 0.8 mm, 0.7 mm, 0.6 mm, 0.5 mm, 0.45 mm, 0.4 mm, 0.35 mm, 0.3 mm, 0.25 mm, 0.2 mm, 0.15 mm, or 0.1 mm from an inner circumference of the intraocular lens housing in the radial direction.

In one embodiment, a clamping portion is disposed at an inner circumferential edge of an intraocular lens housing. In a preferred embodiment, a distance between clamping portions at the inner circumferential edges of the first clamping piece and the second clamping piece is 0.1 mm to 1.5 mm. In a more preferred embodiment, a distance between clamping portions at the inner circumferential edges of the first clamping piece and the second clamping piece is 0.3 to 1.2 mm. Most preferably, a distance between clamping portions at the inner circumferential edges of the first clamping piece and the second clamping piece is 0.5 to 1.0 mm. In a specific embodiment, a distance between clamping portions at the inner circumferential edges of the first clamping piece and the second clamping piece is 0.1 mm, 0.2 mm, 0.3 mm, 0.4 mm, 0.5 mm, 0.6 mm, 0.7 mm, 0.8 mm, 0.9 mm, 1 mm, 1.1 mm, 1.2 mm, 1.3 mm, 1.4 mm, or 1.5 mm. An intraocular lens housing can securely fix an intraocular lens by having such a distance between clamping portions at the inner circumferential edges of the first clamping piece and the second clamping piece. The distance between clamping portions at the inner circumferential edges of the first clamping piece and the second clamping piece can be the same or greater than the distance between portions other than the clamping portions. In a specific embodiment, an intraocular lens fixing device can securely fix an intraocular lens via clamping portions at the inner circumferential edges of the first clamping piece and the second clamping piece of an intraocular lens housing.

In one embodiment, the shortest distance between a center of gravity of a cross-section of the frame and an outer surface of the frame can be changed as needed. In a preferred embodiment, the shortest distance between a center of gravity of a cross-section of the frame and an outer surface of the frame is 0.25 mm. In a specific embodiment, the cross-section of a frame is circular, and the shortest distance between a center of gravity of a cross-section of the frame and an outer surface of the frame is 0.5 mm or greater. In another embodiment, the cross-section of a frame is circular, and the shortest distance between a center of gravity of a cross-section of the frame and an outer surface of the frame is 0.05 mm to 0.3 mm in order to significantly reduce the breakage rate of the fixing device upon insertion of the fixing device. As a result, the time required for device insertion surgery becomes relatively short compared to a device without such a shortest distance. In another embodiment, a frame can have an inner cavity portion. In one embodiment, the cross-section of a frame can be a ring shape.

In one embodiment, the present invention provides a fixing kit for inserting an intraocular lens, and the kit comprise: a) the intraocular lens fixing device of the invention; and b) an injecting instrument for injecting the fixing device. In this regard, the injecting instrument used can be any injecting instrument, as long as a fixing device can be injected.

In another embodiment, the present invention provides a method of inserting an intraocular lens into an eye, and the method comprises: a) inserting the intraocular lens fixing device of the invention into an eye and making a frame of the device support (A) conform to a ciliary sulcus; and b) fixing an intraocular lens to the intraocular lens housing (B) of the intraocular lens fixing device.

In one embodiment, the intraocular lens fixing device is inserted from an incision on an eye in the method of the invention. In still another embodiment, the intraocular lens fixing device is inserted into an eye using an injecting instrument. The methodology of using an injecting instrument can be any methodology that is conventional known. In the method of the invention in one embodiment, the step of inserting the intraocular lens fixing device from an incision on an eye comprises providing an injecting instrument for injecting the intraocular lens fixing device and inserting an intraocular lens fixing device into the eye from an aperture on the eye using the injecting instrument.

In one specific embodiment, the present invention comprises: a) providing a first injecting instrument for injecting the intraocular lens fixing device of any one of the items of the invention; b) inserting the intraocular lens fixing device into an eye from an incision on the eye using the first injecting instrument; c) providing a second injecting instrument for injecting an ocular lens; and d) housing the intraocular lens in the intraocular lens housing (B) of the intraocular lens fixing device from the incision on the eye using the second injecting instrument.

An intraocular lens with any shape or function can be inserted even into an eye with a ruptured or lost lens capsule with such a method of the invention.

PREFERRED EMBODIMENTS

The preferred embodiments of the present invention are described hereinafter. It is understood that the embodiments provided hereinafter are provided to facilitate the understanding of the present invention, so that the scope of the present invention should not be limited by the following descriptions. Thus, it is apparent that those skilled in the art can refer to the descriptions herein to make appropriate modifications within the scope of the present invention. It is also understood that the following embodiments of the invention can be used individually or as a combination.

Embodiment 1

FIG. 1(A) is a cross-sectional view depicting the intraocular lens fixing device according to an embodiment of the invention when installed. FIG. 1(B) is a cross-sectional view schematically depicting an intraocular lens fixed to a natural lens capsule.

With conventional intracapsular fixation, the intraocular lens 3 is fixed within the lens capsule 35 so that the optical portion 31 of the intraocular lens 3 is positioned in a cavity inside the wound formed on the anterior capsule of the lens capsule 35, and the peripheral edge of the lens support 30 is positioned at the equator of the lens capsule 35 in place of a lens removed from the within the lens capsule 35 by surgery as depicted in FIG. 1B.

The intraocular lens fixing device 1 according to the present invention is inserted into an eye with a ruptured or lost lens capsule as depicted in FIG. 1A.

The intraocular lens fixing device 1 is formed with a material having elasticity and flexibility, so that a physician (surgeon) can elastically deform the device 1 to insert the device into the eye from an incision on the eye. The device 1 can be fixed in the eye by holding the device in the ciliary sulcus 36 by utilizing the elastic restoring force of the device 1.

As used herein, front refers to the front with respect to the eye of a patient to whom the intraocular lens 3 is fixed in the eye.

The method of inserting an intraocular lens into an eye of the invention is provided. The insertion method can be materialized using an appropriate operational method (surgical technique) using common general knowledge of ophthalmologists in the art. For example, the method can materialize fixation of an intraocular lens fixing device in an eye by inserting the intraocular lens fixing device of the invention into the eye and making a frame of the device support (A) conform to a ciliary sulcus. It is understood by any ophthalmologist that any appropriate method can be used as such a technique.

Next, b) the step of fixing an intraocular lens to the intraocular lens housing (B) of the intraocular lens fixing device can dispose a desired intraocular lens to a suitable position within the eye. For example, an intraocular lens fixing device can be inserted from an incision on the eye, but this is not limited thereto. A fixing device can be disposed by other methodologies. In a preferred embodiment, an intraocular lens fixing device is inserted into an eye using an injecting instrument. Such an injecting instrument can be any injecting instrument, but is preferably biocompatible and non-toxic or non-stimulatory. For example, an injecting instrument that is compatible with an intraocular lens fixing device is preferred.

For example in one embodiment, the step of inserting the intraocular lens fixing device from an incision on an eye can be materialized by providing an injecting instrument for injecting the intraocular lens fixing device and inserting an intraocular lens fixing device into an eye from an aperture on the eye using the injecting instrument.

In one embodiment, the present invention, for example, comprises: a) providing a first injecting instrument for injecting the intraocular lens fixing device of the invention; b) inserting the intraocular lens fixing device into an eye from an incision on the eye using the first injecting instrument; c) providing a second injecting instrument for injecting an ocular lens; and d) housing the intraocular lens in the intraocular lens housing (B) of the intraocular lens fixing device from the incision on the eye using the second injecting instrument.

Embodiment of Intraocular Lens Fixing Device

The intraocular lens fixing device 1 according to the present invention comprises a device support A and an intraocular lens housing B coupled to the device support A as depicted in FIG. 1A and FIGS. 2 to 4.

The configuration of each member is described hereinafter.

(Device Support)

The device support A is a portion for supporting an intraocular lens fixing device, typically having a frame 2 with a shape that conforms to the ciliary sulcus 36 as depicted in FIG. 2A. The frame 2 is for fixing device the intraocular lens fixing device 1 to the ciliary sulcus 36 by holding (engaging or fitting) the frame 2 to the ciliary sulcus 36. Therefore, the frame 2 can have any shape, as long as it is a shape that conforms to the ciliary sulcus 36. For example, the shape of the frame 2 can be annular, C-shaped, or approximately circular shape that conforms to the ciliary sulcus 36.

The frame 2 is formed in a C-shape in embodiment 1 depicted in FIGS. 1 to 4. The C-shaped frame 2 can be formed by bending or molding an elongated member into a C-shape. When the frame 2 is held in the ciliary sulcus 36, the length of the portion contacting to the ciliary sulcus 36 is preferably half of the entire circumference of the ciliary sulcus 36 or greater, especially 60 to 100% of the entire circumference of the ciliary sulcus 36. Specifically, 22 mm or greater is preferable. Since the frame 2 is formed into a C-shape, a cutout portion 33 is formed on the device support A.

The device 1 does not have a support portion that projects outward as in a conventional device due to the device support A having the frame 2. Thus, the device 1 can be inserted smoothly into the eye through a relatively small incision, such that the incised portion on the eye can be small. Furthermore, the outer shape of the frame 2 is curved so that the eye tissue would not be damaged upon insertion of the device 1. The frame 2 can also have an arcuate shape. By having such a shape, the possibility of being obstructed to pass the inner wall of a wound is reduced when inserting the intraocular lens fixing device 1 into the eye.

The cross-sectional shape of the frame 2 is preferably substantially circular or oval. With such a cross-sectional shape, the outer surface of the frame 2 would have a curvature (curved portion). If the outer surface of the frame 2 has a curvature in this manner, there is no risk of damaging the eye tissue when inserting the device 1 into the eye or fixing device the device to the ciliary sulcus 36.

If the shape of the frame is C-shaped or circular, the diameter of the frame 2 can be 11 to 14 mm. If the shape of the frame is a shape other than annular, C-shaped, or circular shape, the maximum outer diameter of the frame 2 can be 11 to 14 mm. The shortest distance between the center of gravity of a cross-section of the frame 2 and an outer surface of the frame 2 can be 0.05 to 0.3 mm, so that the shape of the frame 2 can have a shape that conforms to the ciliary sulcus 36. Such a shortest distance between center of gravity of a cross-section of the frame 2 and an outer surface of the frame 2 reduces the risk of the device 1 breaking when the device 1 is inserted into the eye or fixed to the ciliary sulcus 36.

(Intraocular Lens Housing)

The intraocular lens housing B is for housing and holding the lens support 30.

The intraocular lens housing B is coupled to the inside of the frame 2. The intraocular lens housing B is comprised of a member that is separate from the frame 2. The intraocular lens housing B and the frame 2 can be coupled directly or with a coupling member, but the intraocular lens housing B is integrally formed with the frame 2 in embodiment 1.

Figure 4:
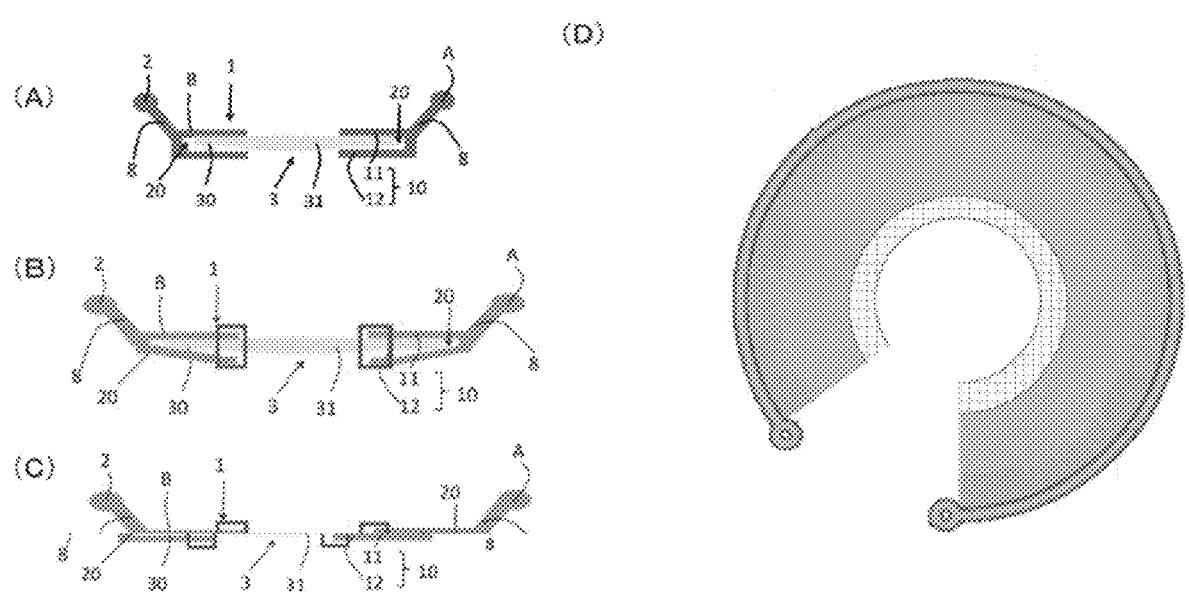
Figure 5:
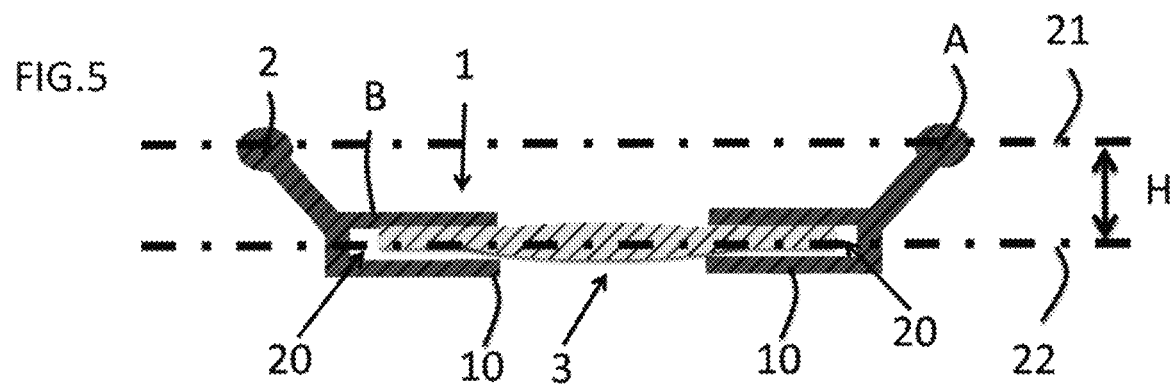
FIG. 5 is a diagram depicting the gap between a first plane and a second plane of the intraocular lens fixing device depicted in FIG. 4(A).

In embodiment 1, the intraocular lens housing B has an extended portion 8 extended inward from the frame 2 of the device support A and a holding piece 10 extended inward from the inside end of the extended portion 8, as depicted in FIGS. 4 and 5. The extended portion 8 is inclined at an angle of 30 degrees to 60 degrees with respect to a first plane 21 formed by the frame 2 of the device support 1. The holding piece 10 has at least a pair of clamping pieces 11, 12 arranged in parallel to hold the lens support 30.

A bag portion 15 for housing and holding the intraocular lens 3 is formed by the extended portion 8 and the clamping pieces 11 and 12. An inner cavity 18 opened to the front surface side and the back surface side of the device 1 is formed inside the bag portion 15. A clamping piece corresponds to the clamping portion in the embodiments of the invention.

As depicted in FIG. 4(A), the bag portion 15 has a space 20 extending in a direction of the frame 2 from the inner cavity 18. The space 20 is formed by the clamping pieces 11, 12 and a wall portion extending from the extended portion 8. The lens support 30 and the circumferential end of the optical portion 31 of the intraocular lens 3 can be housed in the space 20. The clamping pieces 11, 12 of the bag portion 15 are elastically deformable in the direction of a visual axis and can therefore elastically hold the intraocular lens 3 housed in the bag portion 15. The intraocular lens housing B can securely fix the optical portion 31 and the lens support 30 by configuring the distance between the clamping pieces 11 and 12 at the inner circumferential edges of the intraocular lens housing B to be 0.1 mm to 1.5 mm. For this reason, the distance between the clamping pieces 11 and 12 at the inner circumferential edges of the intraocular lens housing B is equal to or greater than a distance between portions other portions of the intraocular lens housing B.

Figure 2:
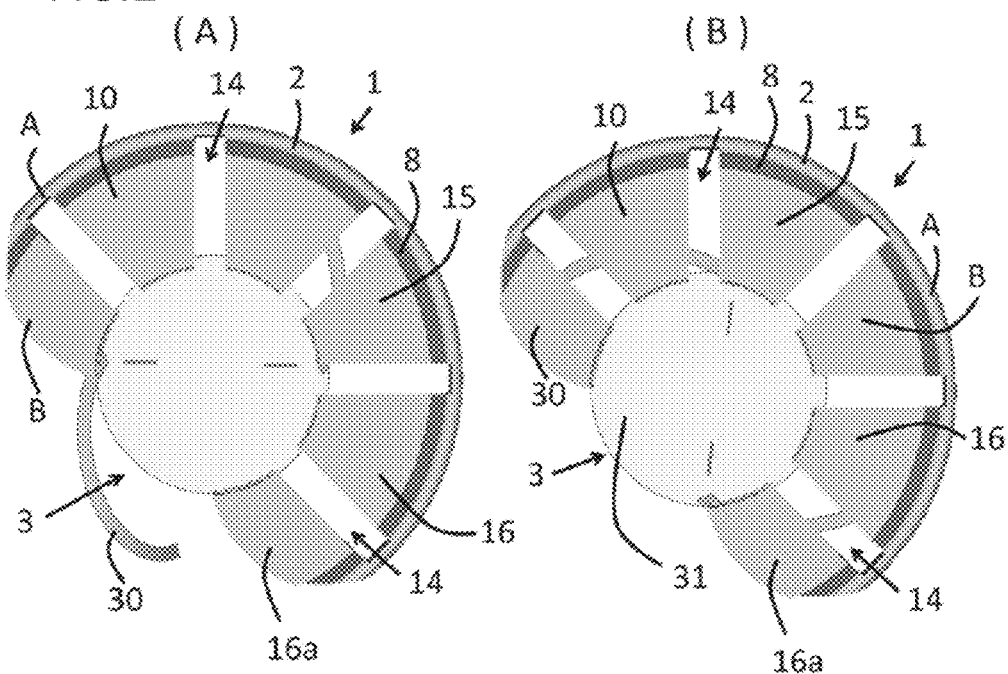
FIG. 2 is a front view of the intraocular lens fixing device depicted in FIG. 1(A).
Figure 3:
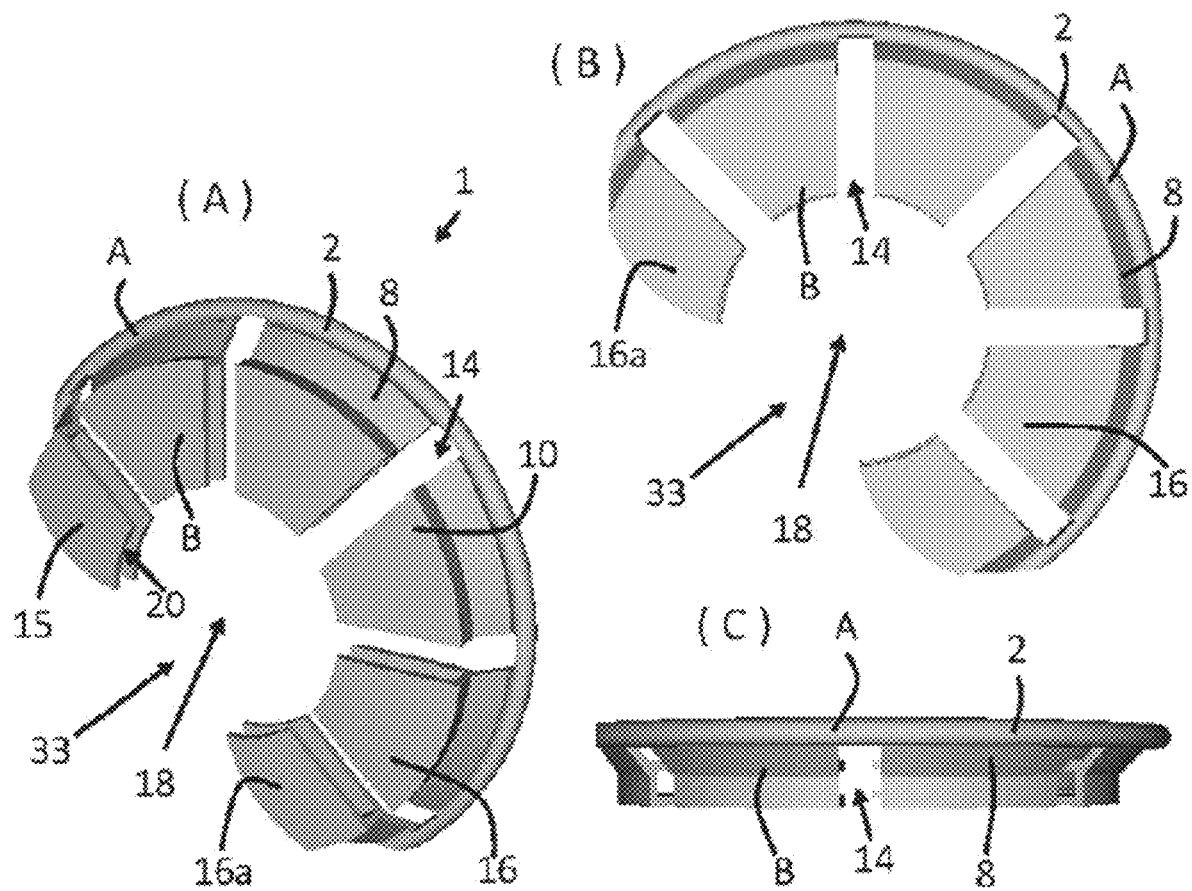

As depicted in FIGS. 2 and 3, a slit 14 extending in the radial direction (direction toward the inside and outside of the device) is formed on the extended portion 8 and the holding piece 10. The bendability of the intraocular lens housing B can be further enhanced by forming the slit 14, which can reduce the risk of breakage of the intraocular lens fixing device 1. While five slits 14 are formed in embodiment 1, about 1 to 10 slits 14 can be formed. The number of slits 14 is preferable multiple, and 3 to 7 is especially preferable. Since the portion constituting the inner circumferential edge of the intraocular lens housing B of the slit 14 can contact the inner wall of wound when inserting the intraocular lens fixing device 1 into the eye, the portion can have an arcuate shape. Furthermore, the intraocular lens housing B can also contact the inner wall of the wound when inserting the intraocular lens fixing device 1 into the eye, the housing can also have an arcuate shape. The possibility of the intraocular lens fixing device 1 being obstructed to pass the inner wall of a wound is reduced when the slit 14 and the intraocular lens housing B have an arcuate shape in this manner.

The width of the slit 14 can be 0.5 mm to 1.0 mm. The length of the holding piece 10 can be 2.5 mm to 3.0 mm.

By forming the slit 14 on the extended portion 8 and the holding piece 10 as described above, the intraocular lens housing B is divided into a plurality of pieces to form elements 16. The outer edge of the element 16 positioned at the end of the plurality of elements 16 is curved to minimize damage to tissue upon insertion of the device 1 into the eye or the like.

The flexibility of the device 1 as well as the operability upon insertion of the device 1 can be improved by forming the slit 14 on the intraocular lens housing B in this manner. In other words, the outer shape of the device 1 can be readily deformed simply by deforming the frame 2. The time required for inserting the intraocular lens fixing device 1 can also be reduced due to the improved flexibility.

Figure 6:
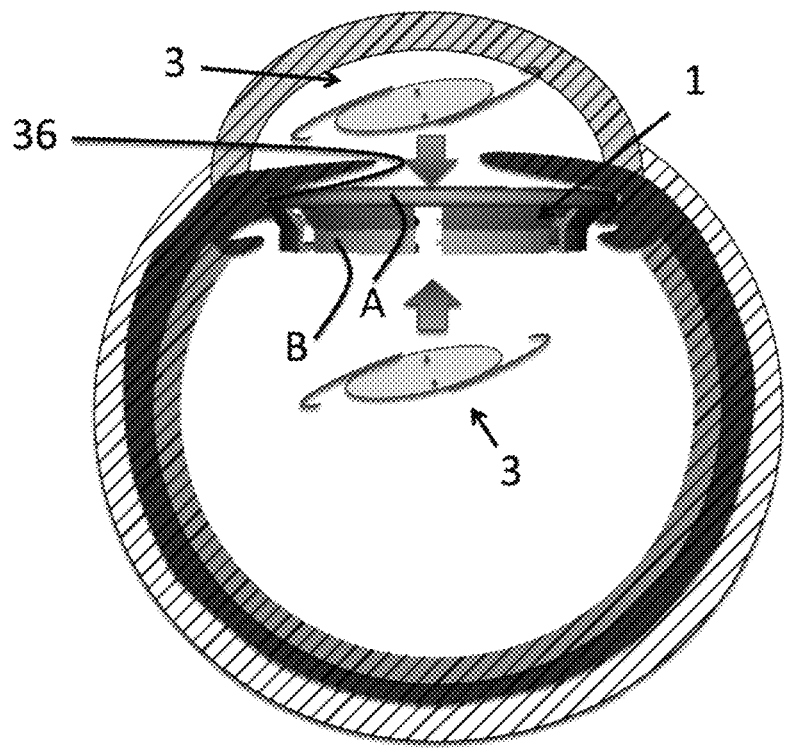
FIG. 6 is a diagram for explaining the action of the intraocular lens fixing device depicted in FIG. 1(A).

The approximately circular inner cavity 18 formed at the center of the intraocular lens housing B has an opening on each of the front side and back side of the intraocular lens housing B. Therefore, the intraocular lens 3 can not only be housed in the housing B of the device 1 from the front, but also from the back of the device 1 as depicted in FIG. 6. The inner diameter of the inner cavity 18 can be about 5.0 mm to 6.0 mm.

As depicted in FIG. 5, the first plane 21 can be formed by the frame 2. In addition, the first plane 22 can be formed by the holding piece 10 of the intraocular lens housing B. The gap H is formed between the first plane 21 and the first plane 22. The gap H is a distance at which there is no change between an angle of refraction of the intraocular lens when the device of the invention is fixed in the eye as depicted in FIG. 1A and the angle of refraction when the intraocular lens 3 is fixed to the natural lens capsule 35 as depicted in FIG. 1B. The gap H can be 1 mm to 3 mm.

Therefore, the distance H1 between the intraocular lens and the front side of the cornea when the device of the invention is mounted (FIG. 1A) would be equal to the distance H2 between the intraocular lens and the front side of the cornea in conventional intraocular capsular fixation (FIG. 1B).

Further, the gap in the front and back of the inner cavity 18 of the capsule is preferably 0.4 mm to 0.7 mm. The thickness of the capsule is preferably 0.1 mm to 0.2 mm.

As described above, the present invention is an artificial lens capsule type fixing device for fixation to a ciliary sulcus. The device is especially preferable to have a disc shape with a diameter of about 12 mm to 14 mm and an inner cavity 18 with a diameter of about 5 mm in the center. The thickness of the entire device is preferably 1 to 2 mm. The inside of the disc has a bag-like structure where an intraocular lens can be inserted, and the intraocular lens can be inserted into the inner cavity 18. Accordingly, a device can be extended and inserted from a 2 mm to 3 mm incision on the eye.

The intraocular lens fixing device 1 is made of a safe and biocompatible material. While biocompatible polymethyl methacrylate (PMMA), polyethyl methacrylate (PEMA), polyhydroxyethyl methacrylate (PHEMA), polypropylene (PP), polyimide, polyvinylidene fluoride (PVDF) or other fluororesin, thermoplastic elastomer, silicone, acrylic material, or the like is preferably used, the device can be made of a material that is transparent and has a certain elasticity, e.g., a biopolymer such as collagen, plastic fiber thread such as nylon, or the like.

While the intraocular lens fixing device 1 is preferably integrally formed with one type of material, the device can also be formed using materials with different properties such as elasticity by bonding or two color molding of the materials.

(Intraocular Lens)

For the intraocular lens 3, different lenses with various conventional forms or lenses with different functions can be used. For example, the invention is compatible with any of the various forms such as the shape of the support of the intraocular lens that has a tentacle form (hapten form), plate form, or the like, intraocular lens optical portion and support that are of different (three pieces) or same (one piece) material or the like (see FIG. 14). A monofocal lens, astigmatism corrective monofocal lens, or multifocal lens can also be used.

The intraocular lens 3 can be inserted and housed into the lens housing B from the inner cavity 18 in the front and back formed on the intraocular lens housing B of the device 1.

Figure 14:
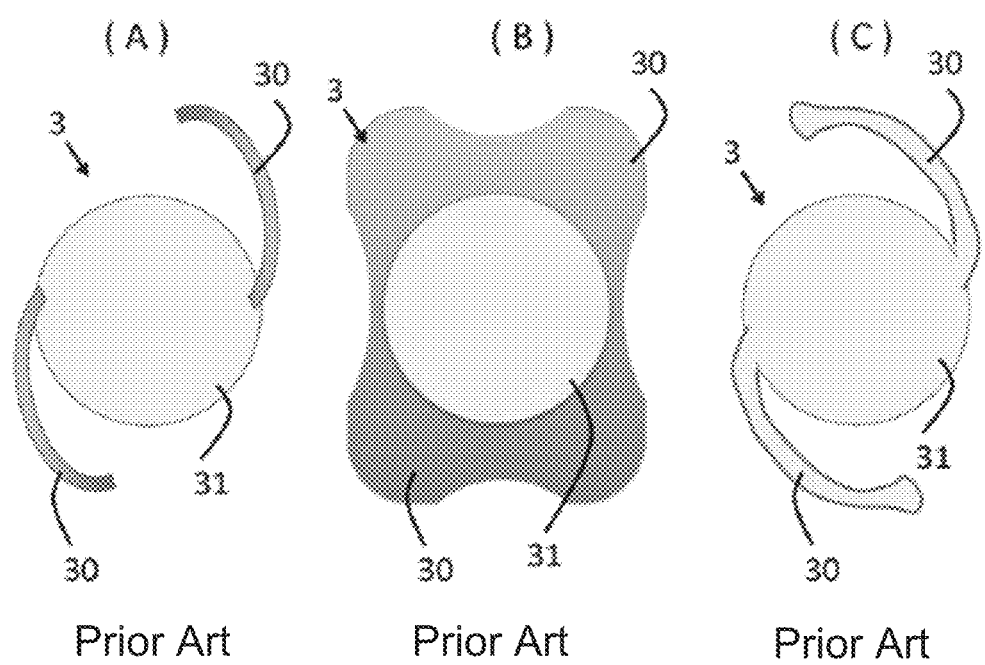
FIGS. 14(A), 14(B), and 14(C) are each front views of a conventional intraocular lens.

As depicted in FIG. 14, the intraocular lens 3 comprises the optical portion (optics) 31 having a lens function and the lens support 30 (tentacle form, hapten) for supporting the optical portion 31.

The optical portion 31 of the intraocular lens 3 is generally a convex lens formed into a disc shape. A plurality of pairs of lens supports 30 projects outward from the opposing positions on the outer circumferential portions thereof.

As depicted in FIG. 2, the intraocular lens 3 is held within the lens housing B by the tip of the lens support 30 engaging with the lens housing B of the device 1. Specifically, the tip of the lens support 30 of the intraocular lens 3 contacts the inner surface of the bag portion 15, and the circumferential end of the optical portion 31 of the intraocular lens 3 is elastically clamped by the pair of clamping pieces 11, 12 as depicted in FIG. 4.

A commercially available product can be used for the intraocular lens 3 housed in the intraocular lens housing B. Examples of the intraocular lens 3 having various refractive properties include (a) normal monofocal lens, (b) astigmatism corrective monofocal lens, and (c) multifocal lens (see FIG. 15).

The intraocular lens 3 can also be formed with the same material as the device 1. Those skilled in the art can select any material. Any material or combination thereof can be used.

The intraocular lens 3 can be formed by integrally forming the lens support 30 of the intraocular lens 3 with the optical portion 31, or by joining the lens support 30, which is separate from the optical portion 31, to the optical portion 31.

The optical portion 31 is a relatively soft portion with a lens function, which is formed into a circular convex lens shape in plan view. The optical portion 31 can have any diameter, as long as the dimension is suitable for inserting the intraocular lens 3 into device 1 in the eye. Specifically, diameter D of the optical portion 31 is preferably in the range of about 5 mm to about 7 mm.

The fixing kit for inserting the intraocular lens of the invention into an eye has the intraocular lens fixing device 1 and an injecting instrument for injecting the fixing device 1.

(Method of Using Intraocular Lens Fixing Device)

Five situations are envisioned as situations for using an intraocular lens fixing device, i.e., (1) the lens is dislocated, (2) the lens capsule is ruptured or the zonule of Zinn is damaged during cataract surgery, (3) the lens capsule is not wholesome post-cataract surgery, and an intraocular lens is not present in the eye, (4) the lens capsule is not wholesome post-cataract surgery, and an intraocular lens is present in the eye, and (5) the intraocular lens that was once fixed intracapsularly is dislocated due to trauma or the like.

The device 1 is inserted into the eye through an incision on the cornea 40 or sclera 43 and a transport portion of the corneal 40 when the lens is removed and the vitreous body behind the lens is excised as needed for (1) and (2) and when the vitreous body is excised as needed in (3), (4), and (5). The device 1 can also be inserted to fix the device to a ciliary sulcus even if an unwholesome lens capsule or zonule of Zinn still remains.

Preferably, the intraocular lens fixing device 1 can be inserted into the eye using an injecting instrument 46 such as an injector.

Figure 13:
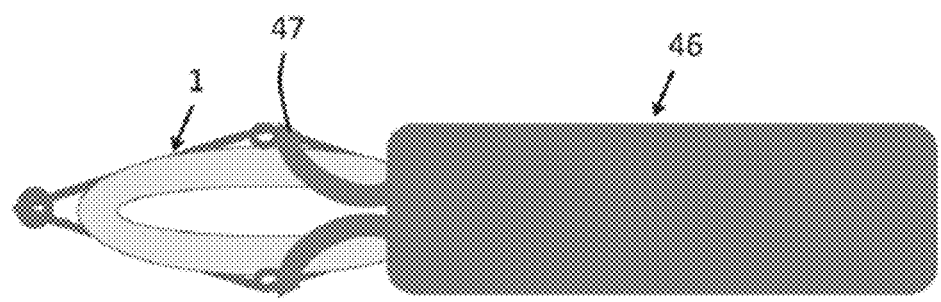
FIG. 13 is a schematic diagram explaining a device clamped at a tip of an injecting instrument

As depicted in FIG. 13, the injecting instrument 46 has a tip operation portion 47 having a function of grasping and compressing (or folding) the device 1 from the outside to reduce the outer shape thereof. The device 1 is inserted into the eye through an incision on the cornea 40 or sclera 43 and a transport portion of the corneal 40 while the device is grasped to reduce the outer diameter.

Figure 12:
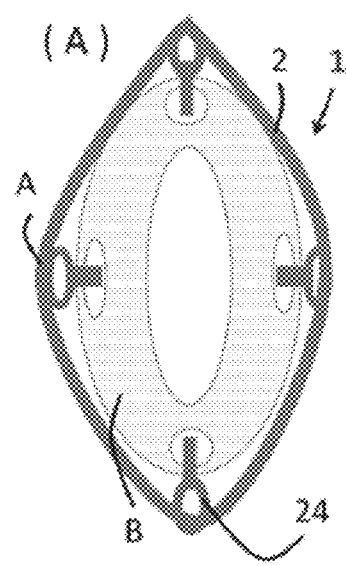
FIGS. 12(A) and 12(B) are a diagram explaining the device shown in FIG. 10 that is deformed when inserted into an incision, and a diagram explaining the device shown in FIG. 1 that is deformed when inserted into an incision.
Figure 12:
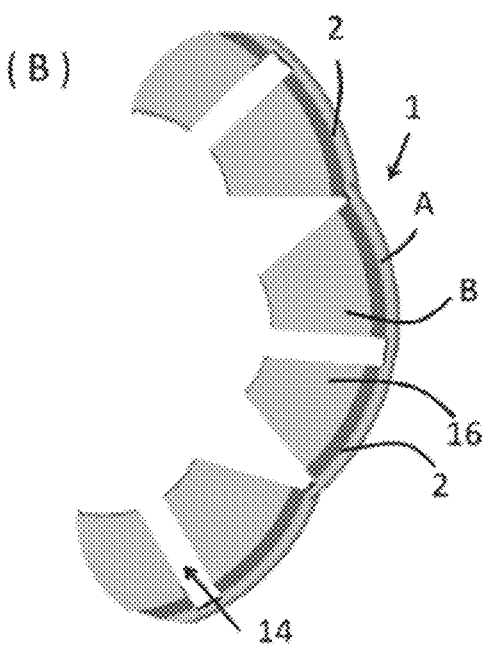

As depicted in FIGS. 3C and 4, the frame 2 is formed to be flat and deformable, so that the device 1 can be deformed into a shape with a narrow width and directly inserted into the eye through an incision on the cornea 40 or sclera 43 and a transport portion of the corneal 40 as depicted in FIGS. 12(A) and 12(B). The width is preferably about 1 mm to about 6 mm and especially preferably about 2 mm to about 3 mm so that the device support A can be readily inserted from the incision.

In this manner, the device 1 is inserted into the eye from an incision on the eye and fixed by making the frame 2 of the device support A conform to the ciliary sulcus.

Next under the situation of (1), (2), or (3), the intraocular lens 3 is inserted into the intraocular lens housing B of the device 1. In this regard, the intraocular lens 3 can be housed in the intraocular lens housing B by deforming or curling up the intraocular lens 3 by using its elasticity (flexibility), inserted into a cartridge or the like, and having the tip of the cartridge reach the front opening of the inner cavity 18 of the intraocular lens housing B through an incision on the cornea 40 or sclera 43 and a transport portion of the corneal 40.

When an intraocular lens is dislocated or shifted in the eye as in (4) or (5), forceps or the like are used to guide and house the intraocular lens 3 into the intraocular lens housing B. When the intraocular lens 3 has fallen to the back of the eye ball such as the cavity of the vitreous body, the intraocular lens 3 can be housed in the bag portion 15 of the intraocular lens housing B from the back opening of the inner cavity 18 as depicted in FIG. 6.

Since the frame 2 is held while contacting many parts of the entire circumference of the ciliary sulcus 36 in this manner, the device 1 is stably fixed to the ciliary sulcus 36.

In the intraocular lens housing B, the lens support 30 contacts the inner surface of the bag portion 15 and the circumferential end of the optical portion 31 of the intraocular lens 3 is clamped by the pair of clamping pieces 11, 12 as shown in FIG. 4, so that the intraocular lens 3 is securely housed and fixed to the intraocular lens housing B.

The intraocular lens housing B has a shape that holds the intraocular lens 3 rotatably about the visual axis. Specifically, as depicted in FIGS. 2(A) and 2(B), the intraocular lens housing B has a shape that forms a complete or incomplete (having slit 14) capsular space 20 with a diameter of about 11 mm to about 13 mm, and a height of about 0.4 mm to about 0.7 mm and can house the intraocular lens 3 while rotating the intraocular lens to any angle about the visual axis.

Such a configuration of the device 1 results in the following effect.

When the astigmatism corrective intraocular lens 3 with an addition function of astigmatism correction is fixed with the device 1, the intraocular lens 3 can be rotated within the device 1 to change the fixing angle to correct the axis of astigmatism of the patient.

The diameter of the inner cavity 18 of the intraocular lens fixing device 1 is designed to be smaller than the diameter of the optical portion 31 of the intraocular lens 3, so that the intraocular lens 3 can be prevented from slipping out after inserting the intraocular lens 3 from the inner cavity 18 of the intraocular lens fixing device 1. Thus, the intraocular lens 3 can be mounted stably.

Therefore, the device 1 is fixed in the eye once the frame is conformed to the ciliary sulcus, so that the intraocular lens 3 can be housed in the intraocular lens housing B of the device 1.

In other words, when the intraocular lens 3 is fixed to the device 1, the intraocular lens 3 can be fixed rotatably about the visual axis in the bag portion 15, so that the lens 3 can be rotated about the visual axis to fix the intraocular lens 3 in the direction matching the direction of astigmatism even when an astigmatism corrective intraocular lens is fixed. Moreover, the device 1 has the bag portion 15 with the inner cavity 18 formed thereon, and the clamping pieces 11, 12 of the bag portion 15 are elastically deformable in the direction of the visual axis. Thus, elastically holding the peripheral end of the optical portion 31 of the intraocular lens 3 housed in the bag portion 15 with the clamping pieces 11 and 12 can ensure that shifting of the intraocular lens within the surface in the direction orthogonal to the visual axis in the bag portion 15 is prevented.

Figure 15:
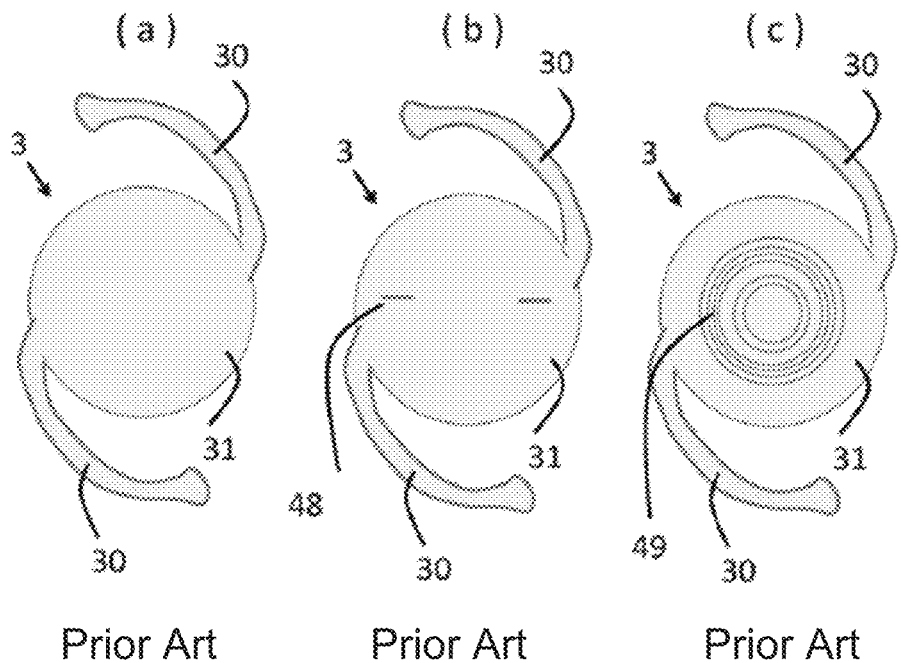
FIGS. 15(A), 15(B), and 15(C) are a front view of a normal monofocal lens, a front view of an astigmatism corrective monofocal lens, and a front view of a multifocal lens.
Figure 16:
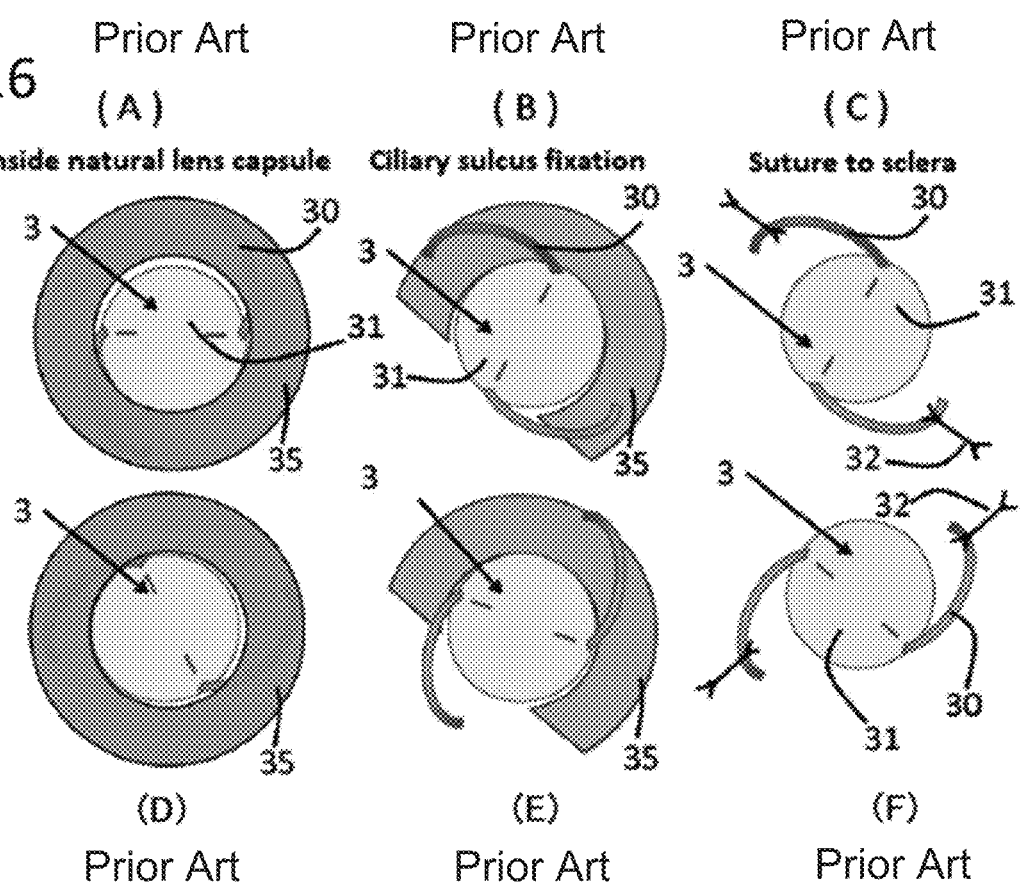
FIGS. 16(A), 16(B), 16(C), 16(D), 16(E), and 16(F) are diagrams depicting problems when fixing an astigmatism correction lens in an eye.
Figure 17:
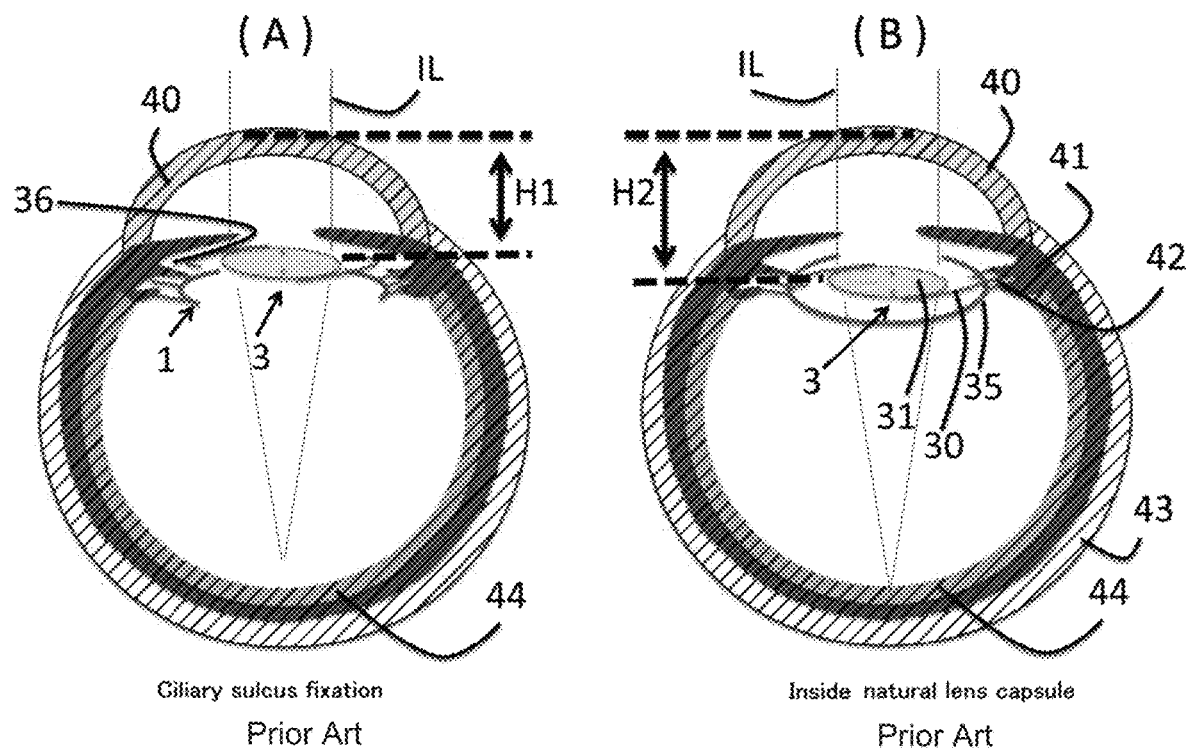
FIGS. 17(A) and 17(B) are diagrams depicting ciliary sulcus fixation of a multifocal intraocular ocular lens and fixation thereof to a natural lens capsule.
Figure 18:
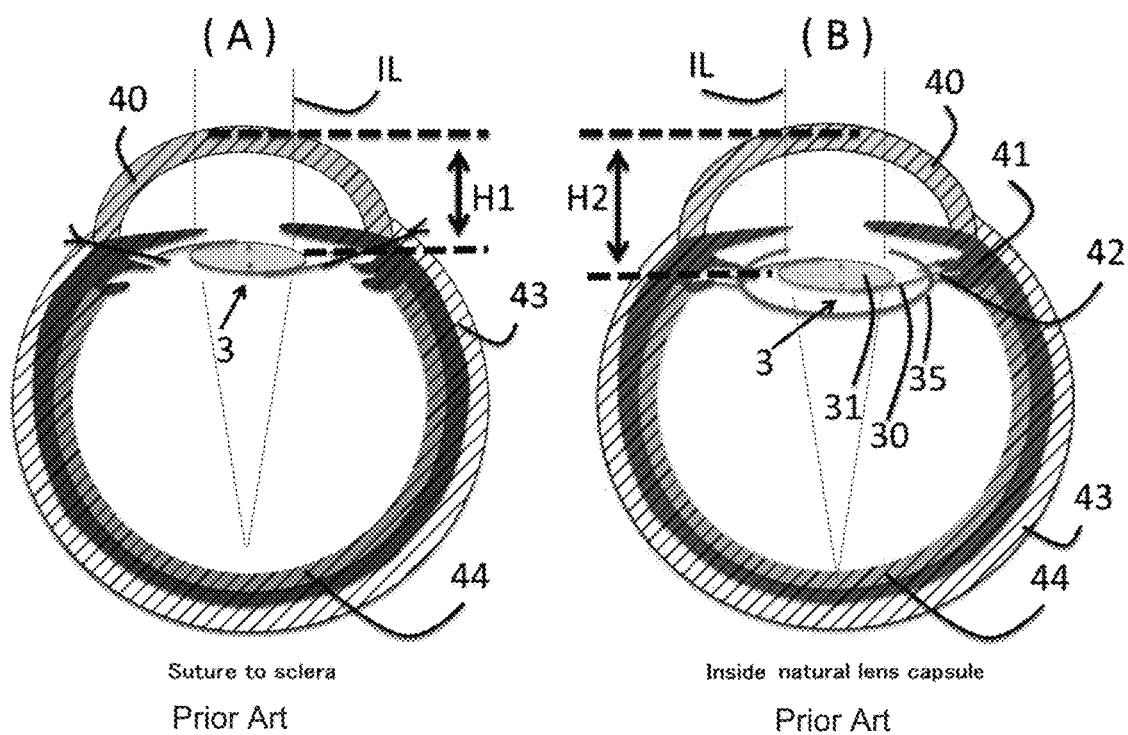
FIGS. 18(A) and 18(B) are diagrams depicting fixation of a multifocal intraocular lens to the sclera and fixation thereof to a natural lens capsule.

After fixing the device 1 to the ciliary sulcus 36, the distance H1 between the intraocular lens 3 housed in the bag portion 15 and the front side of the cornea is nearly equal to the distance H2 between the intraocular lens 3 when fixed inside the natural lens capsule and the front side of the cornea. Thus, the lens 3 can be fixed to the same position on the visual axis as intracapsular fixation even when the multifocal intraocular lens 3 with the support portion 30 as depicted in FIG. 15 is fixed in the eye.

Therefore, there are effects or advantages for not only the patients, but also for physicians and medical institutions, i.e., (1) no restriction on the type of intraocular lens, and (2) no need to change the prescription of the intraocular lens. There is an additional effect for the physicians and medical institutions, i.e., (3) technique and invasive surgery are simple to the same degree as ciliary sulcus fixation or anterior chamber intraocular lens. There is also an additional effect of (4) low manufacturing cost, i.e., low financial burden.

Other Embodiments

Embodiment 2

Figures 7A, 7B, 7C:
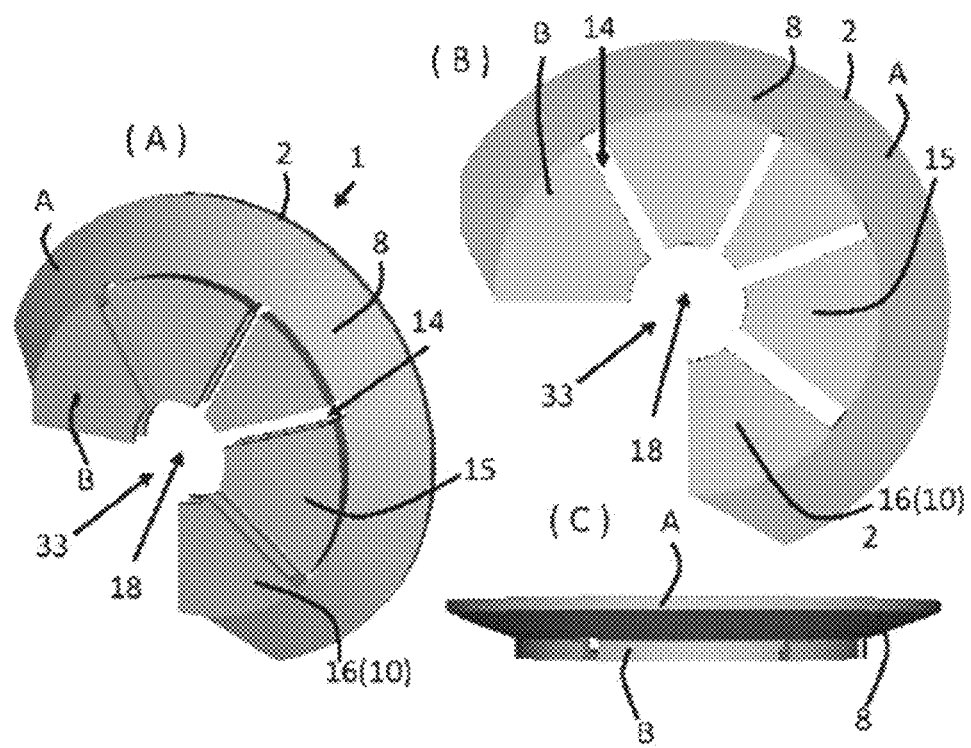
FIGS. 7(A), 7(B), and 7(C) are a perspective view, front view, and side view of the intraocular lens fixing device according to embodiment 2.
Figure 7D:
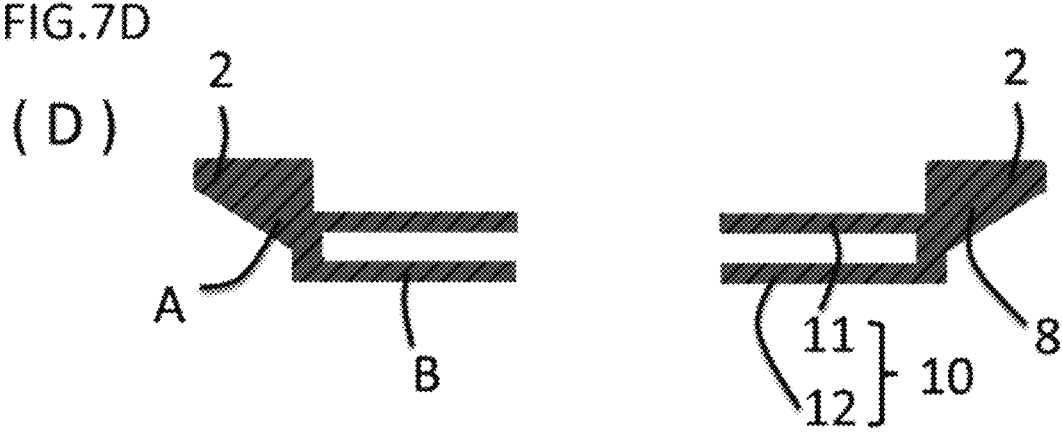
FIG. 7(D) is a cross-sectional view of the intraocular lens fixing device according to embodiment 2.

While embodiment 1 is a representative embodiment, other embodiments can also be used. As depicted in FIG. 7, the device 1 of embodiment 2 is substantially the same as embodiment 1, with the exception of changing the cross-sectional shape of frame 2 to a rectangular or trapezoidal shape and changing the number of slits 14 in embodiment 1.

In this embodiment, the frame 2 of the device support (A) is formed in a nearly C-shaped when viewed from the front. The cross-section of the frame 2 is formed in an approximately trapezoidal shape. The intraocular lens housing B coupled to the device support A has the first clamping piece 11 extended toward the center in the radial direction from the frame 2 and the second clamping piece 12 arranged in parallel to the first clamping piece 11 with a space interposed therebetween. The element 16 of the holding piece 10 is formed by the first clamping piece 11 and the second clamping piece 12. A plurality of the elements 16 of the holding piece 10 is formed inside of the frame 2 via the slit 14.

In this embodiment, four slits 14 are formed on the holding piece 10.

It is understood that this embodiment can also be inserted into the eye in the same manner as embodiment 1, and has the same advantage as embodiment 1.

Embodiment 3

Figures 8A, 8B, 8C:
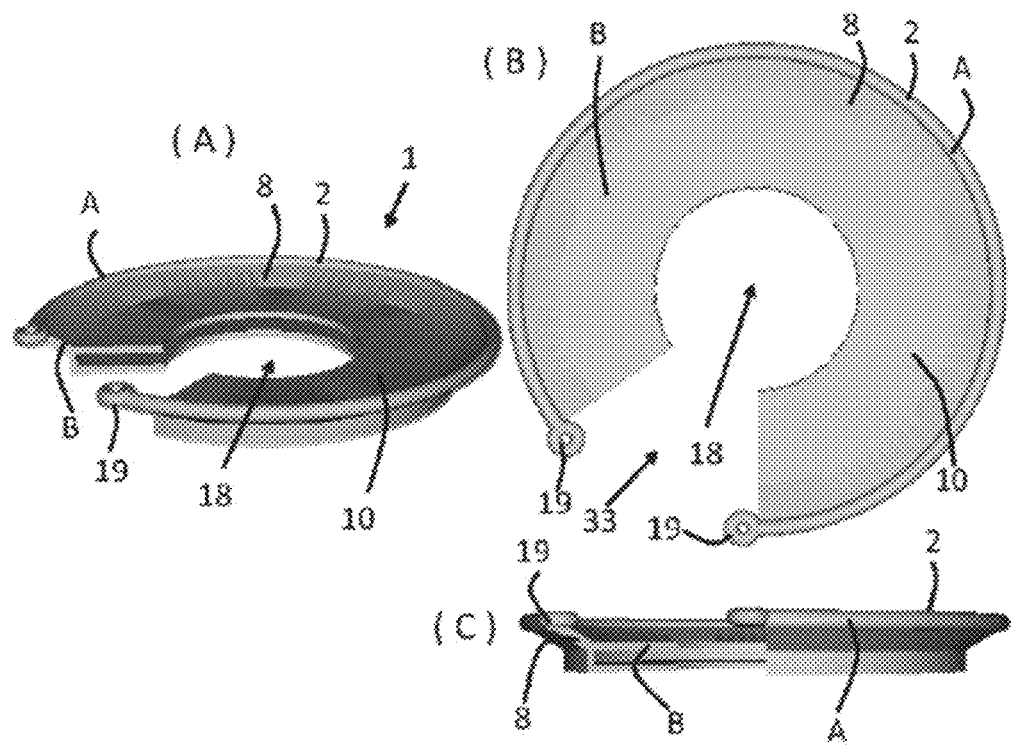
FIGS. 8(A), 8(B), and 8(C) are a perspective view, front view, and partially cutaway side view of the intraocular lens fixing device according to embodiment 3.
Figure 8D:
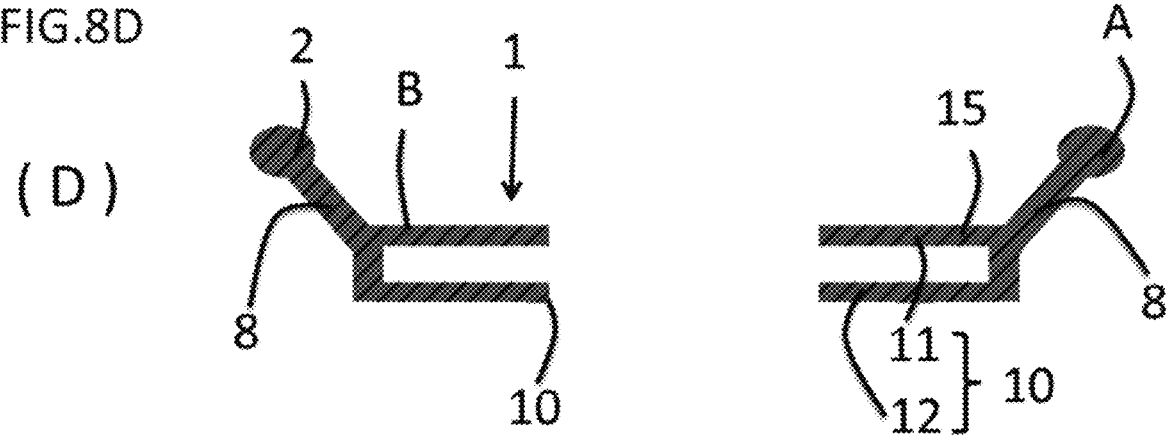
FIG. 8(D) is a cross-sectional view of the intraocular lens fixing device according to embodiment 3.

Embodiment 3 is an embodiment without a slit, which is exemplified in FIG. 8. As depicted in FIG. 8, the device 1 of embodiment 3 is the same as embodiment 1, with the exception of forming operational portions 19 having a through hole on both ends of the frame 2 formed into a C-shape, and not forming the slit 14 on the extended portion 8 of the intraocular lens housing B and on the holding piece 10 extending inside from the inner end of the extended portion 8 in embodiment 1.

In other words, the frame 2 of the device support A is shaped in nearly a C-shape. The cross-section of the frame 2 is formed in a nearly circular shape. The intraocular lens housing B coupled to the device support A has the extended portion 8 extended toward the center in the radial direction from the frame 2 and the holding piece 10 extended toward the inside from the inner end of the extended portion 8. The holding piece 10 has the first and second clamping pieces 11 and 12 arranged in parallel with a space interposed therebetween.

In this embodiment, the device 1 can be inserted into the eye to be fixed to the ciliary sulcus 36 by utilizing a through hole of the operational portion 19 formed on both ends of the frame 2. In other words, the device 1 can be temporarily engaged to the tip of the injecting instrument 46 by locking a projection provided at the tip of the injecting instrument 46 to the through hole, and deformed so that the outer shape is smaller by grabbing the device 1 to insert the device 1 into the eye in such an engaged state.

The diameter of the device 1 (outer diameter of the frame 2) can be about 12 mm to about 14 mm. The thickness of the device 1 can be about 1.0 mm to about 2.0 mm.

It is understood that this embodiment can also be inserted into the eye in the same manner as embodiment 1 or 2 and has the same advantages as embodiments 1 and 2.

Embodiment 4

Figures 9A, 9B, 9C:
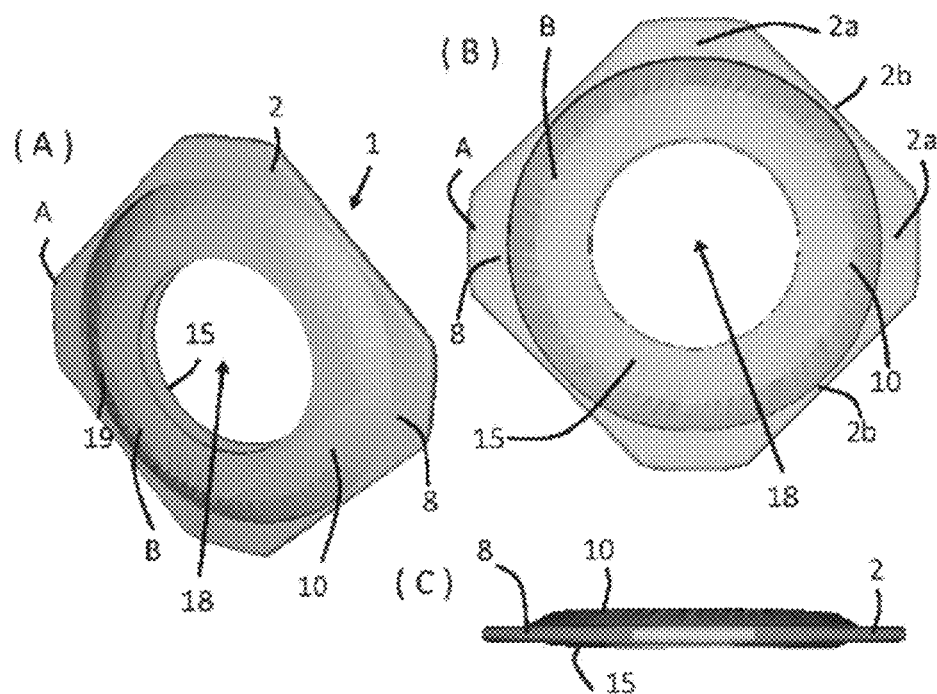
FIGS. 9(A), 9(B), and 9(C) are a perspective view, front view, and partially cutaway side view of the intraocular lens fixing device according to embodiment 4.

Embodiment 4 is an embodiment formed in a nearly square frame with a slit-less shape. As depicted in FIG. 9, the device 1 of embodiment 4 is substantially the same as embodiment, with the exception of forming the frame 2 in an approximately annular shape, and not forming the slit 14 on the extended portion 8 of the intraocular lens housing B and on the holding piece 10 extended to the inside from the inner end of the extended portion 8 in embodiment 1.

In embodiment 4, the frame 2 of the device support A is formed in a nearly square framed annular shape. A region 2a with a wide width is formed at the corners of the square frame. A region 2b with a narrow width is formed between the four broad width portions 2a and 2a.

The intraocular lens housing B coupled to the device support A has an extended portion 8 extended toward the center in the radial direction from the frame 2 and the holding piece 10 extended toward the inside of the extended portion 8. The holding piece 10 has the first and second clamping pieces 11, 12 arranged in parallel with a space interposed therebetween.

The top surface of the extended portion is contiguous with the top surface of the first clamping piece 11. The top surface of the extended portion 8 and the top surface of the first clamping piece 11 form the bag portion 15 having a recess of the front side and a flat center.

For the device 1 with such a configuration, the deformability of the device 1 can be enhanced at the narrow width region 2b of the frame 2. Since the wide width region (support portion) 2a of the frame 2 extends outward, this can ensure that the device 1 is fixed to the ciliary sulcus 36.

The outer diameter (distance between opposing wide width portions 2a) of the device 1 can be about 12 mm to about 14 mm, especially about 13 mm.

The diameter of the bag portion 15 of the device 1 can be about 11 mm, the diameter of the inner cavity 18 of the bag portion 15 can be about 6.0 mm, the distance between the front and back of the inner cavity 18 of the bag portion 15 can be about 0.6 mm, and the thickness of the wall of the bag portion 15 can be about 0.2 mm. The diameter of the flat portion of the bag portion 15 can be about 9 mm.

Figures 9D, 9E:
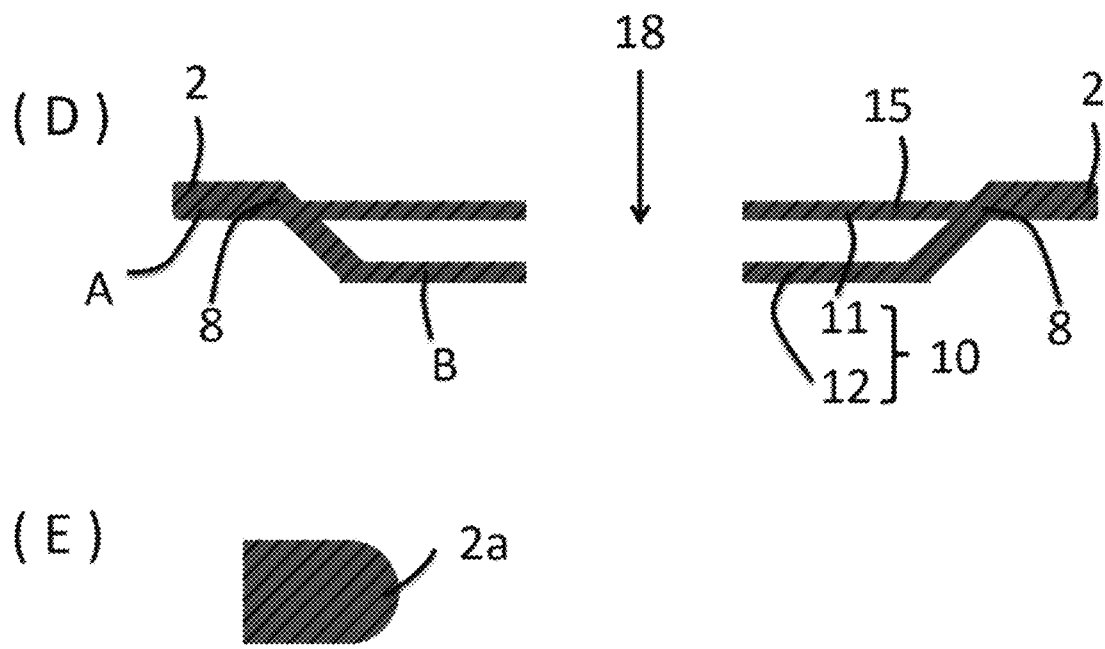
FIGS. 9(D) to 9(E) are a cross-sectional view of the intraocular lens fixing device according to embodiment 4 and a cross-sectional view of the main part of a frame support.

The thickness of the supports (four protruding regions) 2a can be about 0.5 mm, and the thickness of the cross-section of the supports can be about 0.5 mm. As depicted in FIG. 9E, the end on the outer side of the support 2a is formed to be a curved surface (having a curvature).

It is understood that this embodiment can also be inserted into the eye in the same manner as embodiments 1 to 3 and have the same advantages as embodiments 1 to 3.

Embodiment 5

Figures 10A, 10B:
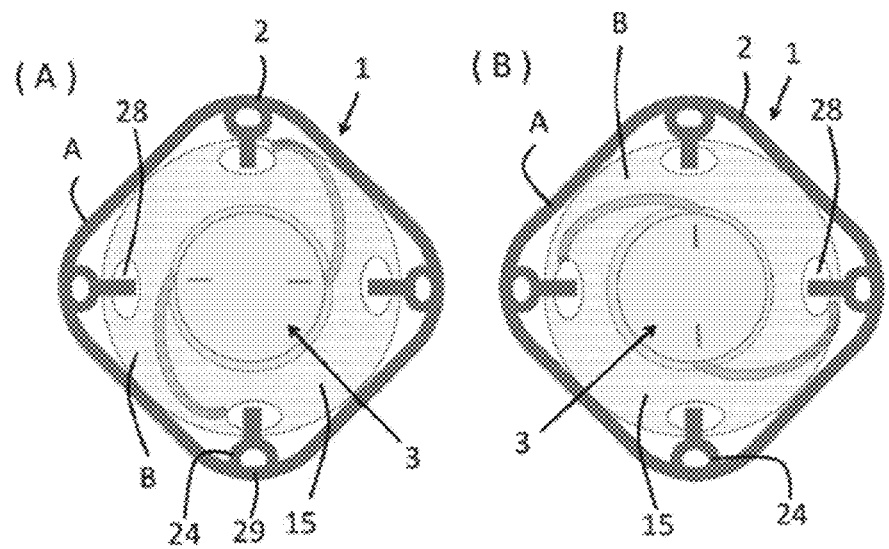
FIGS. 10(A) and 10(B) are a front view of an intraocular lens housed in the intraocular lens fixing device according to embodiment 5, and a front view of the intraocular lens rotated about the visual axis in an intraocular lens housing of the device.
Figures 10C, 10D, 10E:
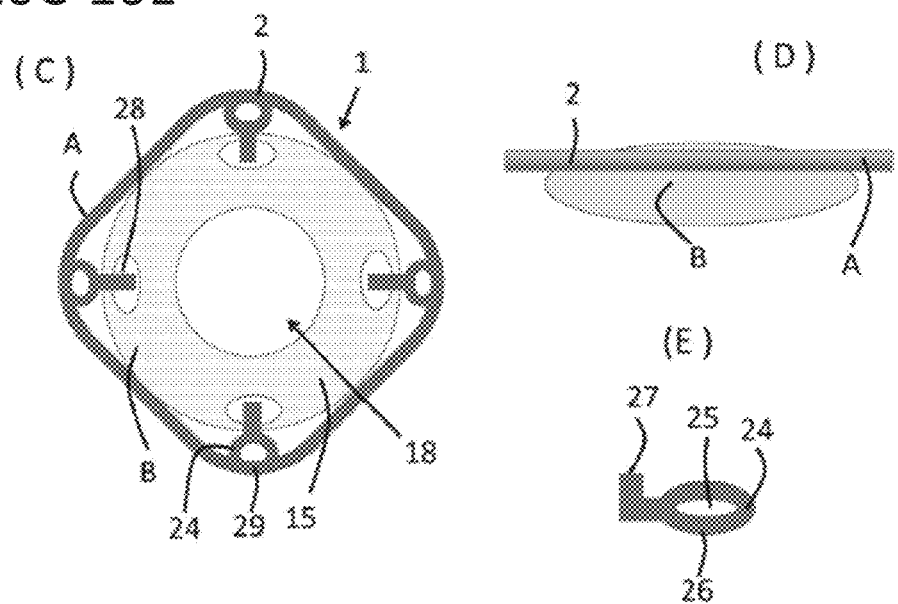
FIGS. 10(C), 10(D), and 10(E) are a front view of the intraocular lens fixing device according to embodiment 5, schematic side view of the device, and an expanded view of a coupling member.

Embodiment 5 is a composite embodiment with a frame coupled to a ring. As depicted in FIG. 10, the device 1 of embodiment 5 is different from embodiment 1 in terms of the frame 2 in embodiment 1 is formed in an annular shape with four corners, and the shape and structure of the intraocular lens housing B coupled to the frame 2.

The intraocular lens housing B has a coupling member 24 coupled to the frame 2, and a ring-shaped bag portion 15 coupled to the coupling member 24 and arranged within the frame 2. The coupling member 24 has a base 26 having a coupling hole 25 that is rotatably fixed to the frame 2 and a hook 27 that extends inside from the base 26.

A support 29 is formed on the protruding region of the square frame 2. The coupling member 24 is coupled to the support 29.

A locking hole 28 is provided at a position corresponding to the coupling member 24 in the periphery of the bag portion 15, and the hook 27 of the coupling member 24 is locked to the locking hole 28.

Figure 11:
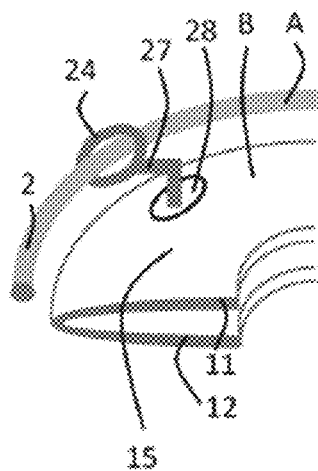
FIG. 11 is an expanded perspective view of the main part of FIG. 10.

As depicted in FIG. 11, the bag portion 15 is formed to have a C-shaped cross-section opened on the inside. Therefore, the bag portion 15 has a pair of clamping pieces 11, 12 arranged in a parallel to the top and bottom with a space interposed therebetween.

Since the support 29 of the frame 2 protrudes outward in the device 1 with such a configuration, it is possible to ensure that the device 1 is fixed to the ciliary sulcus 36. Further, the frame 2 and the intraocular lens housing B are configured as separate members and configured to be coupled. Thus, each member can be relatively readily manufactured. Each member can also be made of materials with different properties from each other. The frame 2 can be made of, for example, PMMA, and the intraocular lens housing B can be made of a more deformable and elastic silicone, acrylic resin, or the like.

The outer diameter of the longest ends of the device 1 (distance between opposing supports) can be about 12 mm. The outer diameter of the bag portion 15 can be about 10 mm. The thickness of the bag portion 15 of the device can be about 2 mm. The diameter of the inner cavity 18 of the bag portion 15 can be about 5.5 mm.

It is understood that this embodiment can also be inserted into the eye in the same manner as embodiments 1 to 4 and has the same advantages as embodiments 1 to 4.

The present invention has been exemplified above with preferred embodiments of the invention, but the present invention should not be interpreted to be limited to these embodiments.

EXAMPLES

Example 1: Trial Production of Novel Intraocular Lens Fixing Device Using a 3D Printer and Utility Verification Test in Animal Eyes To examine the utility of a novel intraocular lens fixing device, an intraocular lens fixing device was designed with a CAD software. An acrylic intraocular lens fixing device was produced using a 3D printer.

Figure 19:
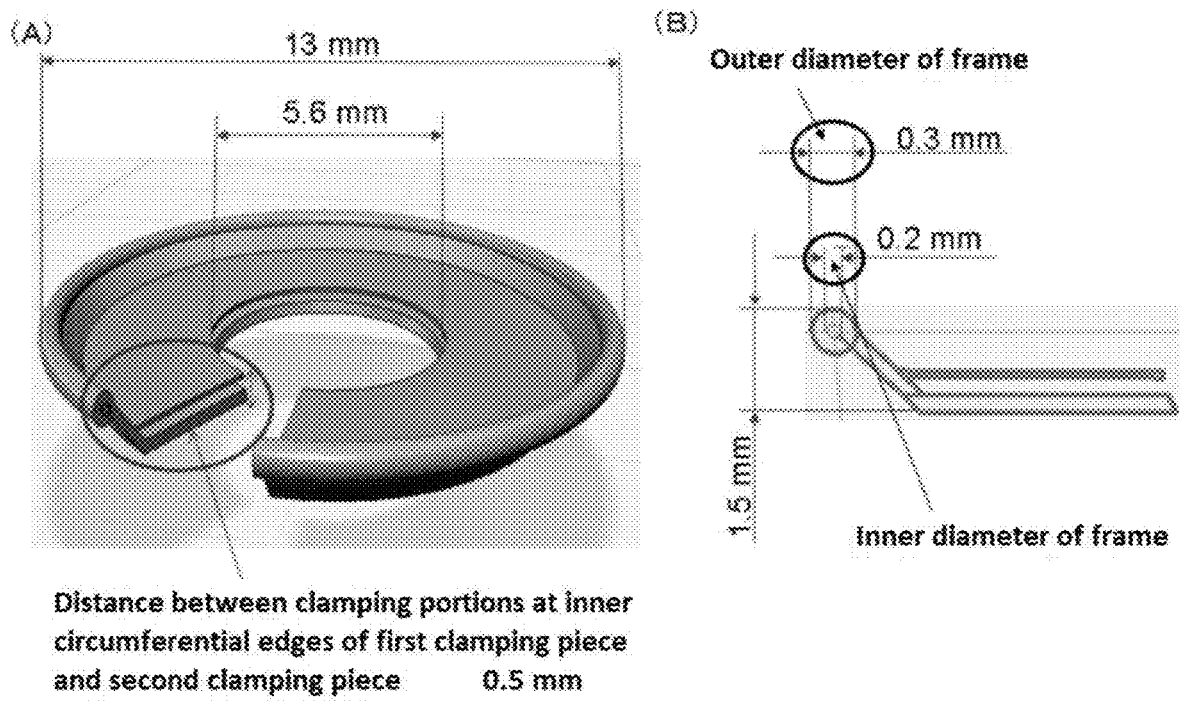
FIGS. 19(A) and 19(B) are a front view and a cross-sectional view of a C-shaped intraocular lens fixing device that was experimentally produced using a 3D printer to study the utility in an animal eye.

Intraocular lens fixing device ver. 1 was produced. As depicted in FIG. 19(A), intraocular lens fixing device ver. 1 has a C-shaped frame and an intraocular lens housing. The inner diameters of the frame and the intraocular lens housing were designed to be 13 mm and 5.6 mm, respectively. The cross-section of the frame was designed to be ring-shaped. The device was designed so that the outer diameter thereof was 0.3 mm, inner diameter was 0.2 mm, the distance between the first plane formed by the frame and the second plane formed by the intraocular lens housing was 1.5 mm, and the distance between the clamping portions at the inner circumferential edges of the first clamping piece and the second clamping piece was 0.5 mm.

The posterior capsule and the entire vitreous body were surgically removed from an extracted swine eye to prepare a posterior capsule ruptured model. Furthermore, the entire lens capsule was removed from another extracted swine eye to prepare a lens capsule full removal model.

The intraocular lens fixing device ver. 1 was inserted so as to rotate a disc from the corneal incision wound to fix an intraocular lens in the prepared posterior capsule ruptured model or lens capsule full removal model.

It was found as a result that the intraocular lens fixing device ver. 1 tended to be obstructed to pass the corneal incision wound and readily broken upon insertion and withdrawal in both the posterior capsule ruptured model or lens capsule full removal model. The distance between the clamping portions at the inner circumferential edges of the first clamping portion and the second clamping portion was narrow, such that the intraocular lens could not be securely fixed. Furthermore, the intraocular lens fixing device ver. 1 lacked flexibility, so that insertion from the corneal incision wound to the deep part inside the eye took a long period of time.

Example 2: Improvement on Novel Intraocular Lens Fixing Device

Based on the result in Example 1, the intraocular lens fixing device was improved to obtain a device capable of fixing an intraocular lens that is readily inserted and withdrawn, and less prone to breaking to prepare intraocular lens fixing device ver. 3.

Figure 20:
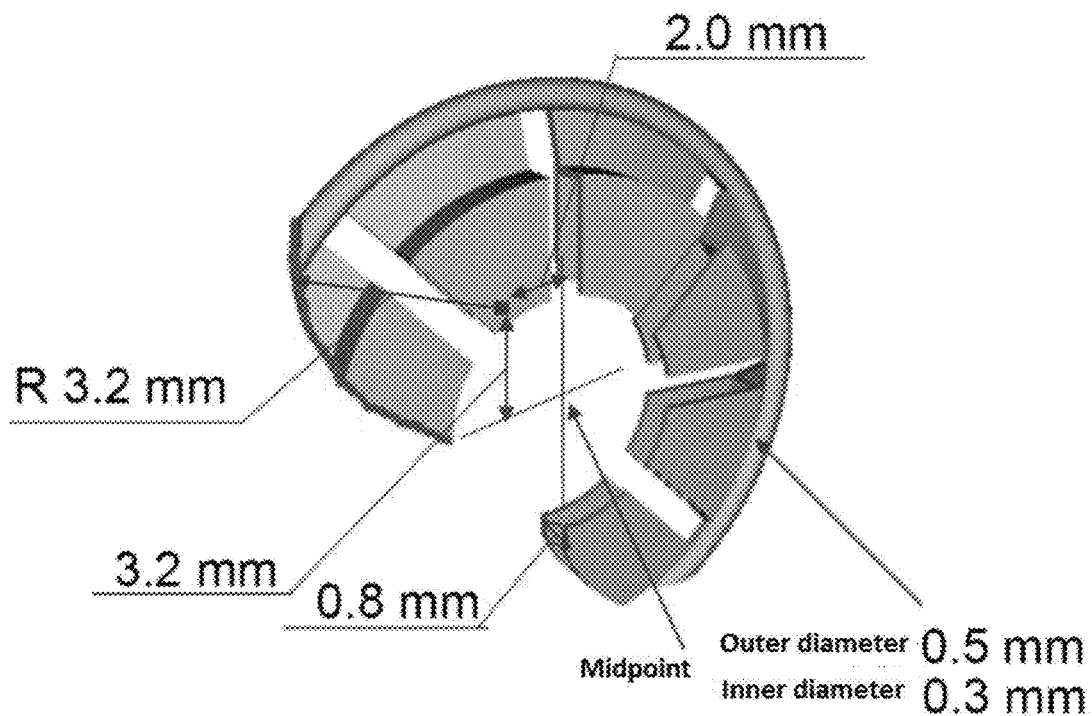
FIG. 20 is a diagram depicting an intraocular lens fixing device having an arcuate tip.

The intraocular lens fixing device ver. 3 was prepared by the same method as the intraocular lens fixing device ver. 1. As depicted in FIG. 20, the intraocular lens fixing device ver. 3 has a C-shaped frame and intraocular lens housing, and the inner diameters of the frame and the intraocular lens housing were designed to be 13 mm and 5.6 mm, respectively. The device was designed so that the outer diameter of the cross-section of the frame was 0.5 mm, the inner diameter was 0.3 mm, the distance between the first plane formed by the frame and the second plane formed by the intraocular lens housing was 1.5 mm, and the distance between the clamping portions at the inner circumferential edges of the first clamping piece and the second clamping piece was 0.8 mm. Furthermore, the tip of the intraocular lens fixing device was cut into an arcuate shape with a radius of 3.2 mm, and five 3.5 mm×0.8 mm slits were added as depicted in FIG. 20.

In the same manner as in Example 1, the intraocular lens fixing device ver. 3 was inserted so as to rotate a disc from the corneal incision wound to fix an intraocular lens in the prepared posterior capsule ruptured model or lens capsule full removal model.

It was found as a result that the intraocular lens fixing device ver. 3 can be inserted into and withdrawn from a cornea incision wound more smoothly and does not break in both the posterior capsule ruptured model and lens capsule full removal model. The intraocular lens fixing device was fixed well to the ciliary sulcus. Since the distance between the clamping portions at the inner circumferential edges of the first and second clamping pieces was widened to a suitable width, an intraocular lens was able to be fixed inside the fixing device well. Furthermore, the intraocular lens fixing device ver. 3 was highly flexible, and the insertion from the corneal incision wound to the deep part inside the eye took a short period of time.

It is understood that the scope of the present invention should be interpreted solely from the scope of Claims. It is understood that those skilled in the art can implement an equivalent scope from the descriptions of the specific preferred embodiments of the invention based on the description of the present invention and common general knowledge.

INDUSTRIAL APPLICABILITY

The intraocular lens fixing device according to the present invention is effective as a fixing device for fixing an intraocular lens implanted into an eye in place of a lens with a damaged function due to cataract.

REFERENCE SIGNS LIST

1 Intraocular lens fixing device
2 Frame
3 Intraocular lens
8 Extended portion
10 Holding piece
11 First clamping piece
12 Second clamping piece
14 Slit
15 Bag portion
A Device support
B Intraocular lens housing

The invention claimed is:

1. An intraocular lens fixing device comprising:
a device support (A); and
an intraocular lens housing (B) coupled to the device support (A);
wherein the device support (A) has a frame with a shape that conforms to a ciliary sulcus and is configured such that the intraocular lens housing (B) is capable of being fixed to the ciliary sulcus,
wherein the intraocular lens housing (B) has an extended portion extended inward from the frame of the device support (A), and a holding piece extended inward from an inside end of the extended portion,
wherein the extended portion is configured to form a gap between a first plane formed by the frame and a second plane formed by the intraocular lens housing (B), the gap having a distance that does not change an angle of refraction as compared to when an intraocular lens is fixed to a natural lens capsule,
wherein the gap is 1 mm to 3 mm,
wherein the outer diameter of the cross-section of the frame is 0.5 mm.

2. The intraocular lens fixing device of claim 1, wherein the intraocular lens housing (B) has a bag portion with an inner cavity formed thereon, and can store an intraocular lens rotatably about a visual axis within the bag portion.

3. The intraocular lens fixing device of claim 2, wherein the bag portion has a clamping portion for holding the intraocular lens.

4. The intraocular lens fixing device of claim 3, wherein the clamping portion is comprised of a pair, and the pair is configured to clamp the intraocular lens.

5. The intraocular lens fixing device of claim 3, wherein the clamping portion is comprised of a plurality of pairs, wherein the plurality of pairs are configured to clamp the intraocular lens.

6. The intraocular lens fixing device of claim 3, wherein the clamping portion is elastically deformable in a direction of a visual axis and can elastically hold the intraocular lens.

7. The intraocular lens fixing device of claim 3, wherein the clamping portion is disposed at inner circumferential edges of a first clamping piece and a second clamping piece of the intraocular lens housing.

8. The intraocular lens fixing device of claim 7, wherein the inner circumferential edges of the first clamping piece and the second clamping piece of the intraocular lens housing are within a range of less than 1.5 mm in a radial direction from an inner circumference of the intraocular lens housing.

9. The intraocular lens fixing device of claim 8, wherein the inner circumferential edges of the first clamping piece and the second clamping piece of the intraocular lens housing are within a range of less than 0.5 mm in a radial direction from an inner circumference of the intraocular lens housing.

10. The intraocular lens fixing device of claim 7, wherein a distance between clamping portions at the inner circumferential edges of the first clamping piece and the second clamping piece is 0.1 mm to 1.5 mm.

11. The intraocular lens fixing device of claim 10, wherein the distance between clamping portions at the inner circumferential edges of the first clamping piece and the second clamping piece is 0.3 mm to 1.2 mm.

12. The intraocular lens fixing device of claim 11, wherein the distance between clamping portions at the inner circumferential edges of the first clamping piece and the second clamping piece is 0.5 mm to 1.0 mm.

13. The intraocular lens fixing device of claim 1, wherein a distance between clamping portions of the inner circumferential edges of the first clamping piece and the second clamping piece is equal to or greater than a distance between portions other than the clamping portions of the intraocular lens housing.

14. An intraocular lens fixing device comprising:
a device support (A); and
an intraocular lens housing (B) coupled to the device support (A);
wherein the device support (A) has a frame with a shape that conforms to a ciliary sulcus and is configured such that the intraocular lens housing (B) is capable of being fixed to the ciliary sulcus,
wherein the intraocular lens housing (B) has an extended portion extended inward from the frame of the device support (A), and a holding piece extended inward from an inside end of the extended portion,
wherein the extended portion is configured to form a gap between a first plane formed by the frame and a second plane formed by the intraocular lens housing (B), the gap having a distance that does not change an angle of refraction as compared to when an intraocular lens is fixed to a natural lens capsule,
wherein the gap is 1 mm to 3 mm,
wherein the shortest distance between a center of gravity of a cross-section of the frame and an outer surface of the frame is 0.05 mm to 0.3 mm.

15. The intraocular lens fixing device of claim 2, wherein the bag portion has a space extending in a direction of the frame from the inner cavity.

16. The intraocular lens fixing device of claim 15, wherein the space can at least partially house an optical portion of the intraocular lens.

17. The intraocular lens fixing device of claim 1, wherein the frame has an arcuate portion.

18. The intraocular lens fixing device of claim 17, wherein the frame has two or more arcuate portions.

19. The intraocular lens fixing device of claim 18, wherein the frame has three or more arcuate portions.

20. The intraocular lens fixing device of claim 1, wherein the frame has an annular shape, a C-shape, or an approximately circular shape.

21. The intraocular lens fixing device of claim 1, wherein the device support has a length sufficient such that it is capable of contacting half of a circumference of a ciliary sulcus or greater.

22. The intraocular lens fixing device of claim 1, wherein the intraocular lens housing (B) has an elastically deformable structure.

23. The intraocular lens fixing device of claim 1, wherein the intraocular lens housing (B) has a slit that is long in a radial direction of the frame.

24. The intraocular lens fixing device of claim 1, wherein the intraocular lens housing (B) is comprised of an elastically deformable material.

25. The intraocular lens fixing device of claim 1, wherein the device support is deformable to a flat shape so as to allow insertion from an incision.

26. The intraocular lens fixing device of claim 1, wherein the intraocular lens housing (B) has a C-shape, and an arcuate portion at a tip thereof.

27. The intraocular lens fixing device of claim 26, wherein the intraocular lens housing (B) has two or more arcuate portions.

28. The intraocular lens fixing device of claim 27, wherein the intraocular lens housing (B) has three or more arcuate portions.

29. The intraocular lens fixing device of claim 1, wherein the device support has a size which allows insertion from an incision.

30. The intraocular lens fixing device of claim 1, wherein a cross-sectional shape of the frame is circular or oval.

31. The intraocular lens fixing device of claim 1, wherein an outer surface of the frame has a curvature.

32. The intraocular lens fixing device of claim 1, wherein the holding piece has a pair of clamping pieces arranged in parallel to hold an intraocular lens.

33. The intraocular lens fixing device of claim 1, wherein the extended portion is inclined at an angle of 30 degrees to 60 degrees with respect to a first plane formed by the frame of the support.

34. The intraocular lens fixing device of claim 1, having a shape which allows injection with an injecting instrument.

35. A fixing kit for inserting an intraocular lens, comprising:
a) the intraocular lens fixing device of claim 1; and
b) an injecting instrument for injecting the fixing device.

36. The intraocular lens fixing device of claim 1, wherein the intraocular lens housing (B) has five slits that are long in a radial direction of the frame.

37. The intraocular lens fixing device of claim 1, wherein the inner diameter of the frame is 13 mm.

38. The intraocular lens fixing device of claim 1, wherein the intraocular lens housing (B) has five slits that are long in a radial direction of the frame, and wherein the inner diameter of the frame is 13 mm.

39. An intraocular lens fixing device comprising:
a device support (A); and
an intraocular lens housing (B) coupled to the device support (A);
wherein the device support (A) has a frame with a shape that conforms to a ciliary sulcus and is configured such that the intraocular lens housing (B) is capable of being fixed to the ciliary sulcus,
wherein the intraocular lens housing (B) has an extended portion extended inward from the frame of the device support (A), and a holding piece extended inward from an inside end of the extended portion, wherein the extended portion is configured to form a gap between a first plane formed by the frame and a second plane formed by the intraocular lens housing (B), the gap having a distance that does not change an angle of refraction as compared to when an intraocular lens is fixed to a natural lens capsule, wherein the gap is 1 mm to 3 mm, wherein the intraocular lens housing (B) has five slits that are long in a radial direction of the frame, and wherein the outer diameter of the cross-section of the frame is 0.5 mm.

40. An intraocular lens fixing device comprising:

a device support (A); and an intraocular lens housing (B) coupled to the device support (A);

wherein the device support (A) has a frame with a shape that conforms to a ciliary sulcus and is configured such that the intraocular lens housing (B) is capable of being fixed to the ciliary sulcus, wherein the intraocular lens housing (B) has an extended portion extended inward from the frame of the device support (A), and a holding piece extended inward from an inside end of the extended portion, wherein the extended portion is configured to form a gap between a first plane formed by the frame and a second plane formed by the intraocular lens housing (B), the gap having a distance that does not change an angle of refraction as compared to when an intraocular lens is fixed to a natural lens capsule, wherein the gap is 1 mm to 3 mm, wherein the outer diameter of the cross-section of the frame is 0.5 mm, and wherein the inner diameter of the frame is 13 mm.

41. An intraocular lens fixing device comprising:

a device support (A); and an intraocular lens housing (B) coupled to the device support (A);

wherein the device support (A) has a frame with a shape that conforms to a ciliary sulcus and is configured such that the intraocular lens housing (B) is capable of being fixed to the ciliary sulcus, wherein the intraocular lens housing (B) has an extended portion extended inward from the frame of the device support (A), and a holding piece extended inward from an inside end of the extended portion, wherein the extended portion is configured to form a gap between a first plane formed by the frame and a second plane formed by the intraocular lens housing (B), the gap having a distance that does not change an angle of refraction as compared to when an intraocular lens is fixed to a natural lens capsule, wherein the gap is 1 mm to 3 mm, wherein the outer diameter of the cross-section of the frame is 0.5 mm, wherein the intraocular lens housing (B) has five slits that are long in a radial direction of the frame and wherein the inner diameter of the frame is 13 mm.

42. An intraocular lens fixing device comprising:

a device support (A); and an intraocular lens housing (B) coupled to the device support (A);

wherein the device support (A) has a frame with a shape that conforms to a ciliary sulcus and is configured such that the intraocular lens housing (B) is capable of being fixed to the ciliary sulcus, wherein the intraocular lens housing (B) has an extended portion extended inward from the frame of the device support (A), and a holding piece extended inward from an inside end of the extended portion, wherein the extended portion is configured to form a gap between a first plane formed by the frame and a second plane formed by the intraocular lens housing (B), the gap having a distance that does not change an angle of refraction as compared to when an intraocular lens is fixed to a natural lens capsule, wherein the gap is 1 mm to 3 mm, wherein the intraocular lens housing (B) has a bag portion with an inner cavity formed thereon, and can store an intraocular lens rotatably about a visual axis within the bag portion, wherein the bag portion has a clamping portion for holding the intraocular lens, wherein the clamping portion is comprised of a plurality of pairs, wherein the plurality of pairs are configured to clamp the intraocular lens, wherein the clamping portion is elastically deformable in a direction of a visual axis and can elastically hold the intraocular lens, wherein the clamping portion is disposed at inner circumferential edges of a first clamping piece and a second clamping piece of the intraocular lens housing, wherein the inner circumferential edges of the first clamping piece and the second clamping piece of the intraocular lens housing are within a range of less than 1.5 mm in a radial direction from an inner circumference of the intraocular lens housing, wherein the distance between clamping portions at the inner circumferential edges of the first clamping piece and the second clamping piece is 0.5 mm to 1.0 mm, wherein a distance between clamping portions of the inner circumferential edges of the first clamping piece and the second clamping piece is equal to or greater than a distance between portions other than the clamping portions of the intraocular lens housing, wherein the shortest distance between a center of gravity of a cross-section of the frame and an outer surface of the frame is 0.05 mm to 0.3 mm, wherein the bag portion has a space extending in a direction of the frame from the inner cavity, wherein the space can at least partially house an optical portion of the intraocular lens, wherein the frame has three or more arcuate portions, wherein the frame has an annular shape, a C-shape, or an approximately circular shape, wherein the device support has a length sufficient such that it is capable of contacting half of a circumference of a ciliary sulcus or greater, wherein the intraocular lens housing (B) has an elastically deformable structure, wherein the intraocular lens housing (B) is comprised of an elastically deformable material, wherein the device support is deformable to a flat shape so as to allow insertion from an incision, wherein the intraocular lens housing (B) has a C-shape, and an arcuate portion at a tip thereof, wherein the intraocular lens housing (B) has three or more arcuate portions, wherein the device support has a size which allows insertion from an incision, wherein a cross-sectional shape of the frame is circular or oval, wherein an outer surface of the frame has a curvature, wherein the holding piece has a pair of clamping pieces arranged in parallel to hold an intraocular lens,
wherein the extended portion is inclined at an angle of 30 degrees to 60 degrees with respect to a first plane formed by the frame of the support,
wherein the intraocular lens fixing device has a shape which allows injection with an injecting instrument,
wherein the outer diameter of the cross-section of the frame is 0.5 mm,
wherein the intraocular lens housing (B) has five slits that are long in a radial direction of the frame.

* * * * *